(12) United States Patent
Susi

(10) Patent No.: US 7,553,295 B2
(45) Date of Patent: Jun. 30, 2009

(54) LIQUID INFUSION APPARATUS

(75) Inventor: Roger E. Susi, Wintor Park, FL (US)

(73) Assignee: IRadimed Corporation, Winter Park, FL (US)

( * ) Notice: Subject to any disclaimer, the term of this patent is extended or adjusted under 35 U.S.C. 154(b) by 397 days.

(21) Appl. No.: 11/271,705

(22) Filed: Nov. 10, 2005

(65) Prior Publication Data

US 2006/0173412 A1 Aug. 3, 2006

(51) Int. Cl.
*A61M 1/00* (2006.01)
*H02K 33/00* (2006.01)

(52) U.S. Cl. .................................. 604/151; 318/114

(58) Field of Classification Search ............. 604/890.1, 604/131, 151; 318/114
See application file for complete search history.

(56) References Cited

U.S. PATENT DOCUMENTS

| | | | |
|---|---|---|---|
| 2,696,963 A | 12/1954 | Shepherd | |
| 4,344,743 A * | 8/1982 | Bessman et al. | 310/324 |
| 4,564,812 A | 1/1986 | Van Dijk | |
| 4,689,043 A | 8/1987 | Bisha | |
| 4,798,590 A | 1/1989 | O'Leary | |
| 4,857,048 A | 8/1989 | Simons et al. | |
| 4,888,514 A | 12/1989 | Takahashi et al. | |
| 5,021,700 A | 6/1991 | Takahashi et al. | |
| 5,059,173 A | 10/1991 | Sacco | |
| 5,130,619 A | 7/1992 | Izuno | |
| 5,494,036 A | 2/1996 | Uber et al. | |
| 5,522,799 A | 6/1996 | Furukawa | |
| 5,553,619 A | 9/1996 | Prince | |
| 5,563,464 A | 10/1996 | Okubu et al. | |
| 5,713,856 A | 2/1998 | Eggers et al. | |

(Continued)

FOREIGN PATENT DOCUMENTS

DE 197 147 11 A1 10/1998

(Continued)

OTHER PUBLICATIONS

International Search Report for PCT Application No. PCT/US03/19334, Mar. 15, 2004.

(Continued)

*Primary Examiner*—Kevin C. Sirmons
*Assistant Examiner*—Elizabeth R MacNeill
(74) *Attorney, Agent, or Firm*—Knobbe, Martens, Olson & Bear LLP

(57) ABSTRACT

Liquid infusion apparatus includes non-magnetic materials in a pumping structure and ultrasonic drive motor therefor, and in a controller that supplies drive signals to the motor to facilitate convenient operation in intense magnetic fields without distorting the magnetic fields and without radiating objectionable radio-frequency interference. A non-MRI-compatible liquid infusion apparatus is temporarily replaced with MRI-compatible, non-magnetic liquid infusion apparatus without disconnecting a patient from an installed intravenous infusion set to continue infusing liquid within the MRI environment. The pumping apparatus operates on a segment of a liquid conduit that is mounted in tension between a linear peristaltic pump and platen, with associated safety interlocks to assure proper operation of infusing liquid into a patient compatibly with conditions in an MRI environment. Drive circuitry generates low-harmonic signals for operating the ultrasonic motor at variable speeds to compensate for flow rate discontinuities through the peristaltic pumping cycles.

11 Claims, 20 Drawing Sheets

U.S. PATENT DOCUMENTS

| | | | |
|---|---|---|---|
| 5,770,181 | A | 6/1998 | Kirkland |
| 5,864,331 | A | 1/1999 | Anand et al. |
| 5,967,484 | A | 10/1999 | Morris |
| 6,052,614 | A | 4/2000 | Morris et al. |
| 6,117,115 | A | 9/2000 | Hill et al. |
| 6,193,480 | B1 * | 2/2001 | Butterfield ............... 417/477.1 |
| 6,198,285 | B1 | 3/2001 | Kormos et al. |
| 6,213,723 | B1 | 4/2001 | Danby et al. |
| 6,213,738 | B1 | 4/2001 | Danby et al. |
| 6,213,739 | B1 | 4/2001 | Phallen et al. |
| 6,221,045 | B1 | 4/2001 | Duchon et al. |
| 6,230,041 | B1 | 5/2001 | Prince |
| 6,240,311 | B1 | 5/2001 | Prince |
| 6,243,600 | B1 | 6/2001 | Prince |
| 6,316,862 | B1 | 11/2001 | Nakata et al. |
| 6,418,337 | B1 | 7/2002 | Torchia et al. |
| 6,463,318 | B2 | 10/2002 | Prince |
| 6,503,221 | B1 | 1/2003 | Briggs et al. |
| 6,641,562 | B1 | 11/2003 | Peterson |
| 6,643,537 | B1 | 11/2003 | Zatezalo et al. |
| 6,659,978 | B1 | 12/2003 | Kasuga et al. |
| 6,881,043 | B2 | 4/2005 | Barak |
| 6,889,072 | B2 | 5/2005 | Prince |
| 2002/0010397 | A1 | 1/2002 | Prince |
| 2002/0115933 | A1 | 8/2002 | Duchon et al. |
| 2002/0165503 | A1 | 11/2002 | Morris |
| 2003/0014035 | A1 | 1/2003 | Trombley et al. |
| 2003/0171670 | A1 | 9/2003 | Gumb et al. |
| 2004/0030281 | A1 | 2/2004 | Goble et al. |
| 2004/0176984 | A1 | 9/2004 | White et al. |
| 2005/0256388 | A1 | 11/2005 | Susi |
| 2006/0042633 | A1 | 3/2006 | Bishop et al. |
| 2006/0079758 | A1 | 4/2006 | Susi |
| 2006/0173412 | A1 | 8/2006 | Susi |

FOREIGN PATENT DOCUMENTS

| | | |
|---|---|---|
| EP | 0 447 985 A | 9/1991 |
| EP | 0 602 635 A1 | 6/1994 |
| EP | 0 606 099 A2 | 7/1994 |
| JP | 7 178 169 | 7/1995 |
| WO | WO 02/00276 | 1/2002 |
| WO | WO 03/105925 A2 | 12/2003 |

OTHER PUBLICATIONS

International Search Report for PCT Application No. PCT/US05/36641, Jun. 12, 2006.

International Search Report for PCT Application No. PCT/US0319334, Mar. 26, 2007.

Partial International Search Report for PCT Application No. PCT/US2006/043816, Apr. 25, 2007.

International Search Report for PCT Application No. PCT/US2006/043816, date of mailing Sep. 21, 2007.

* cited by examiner

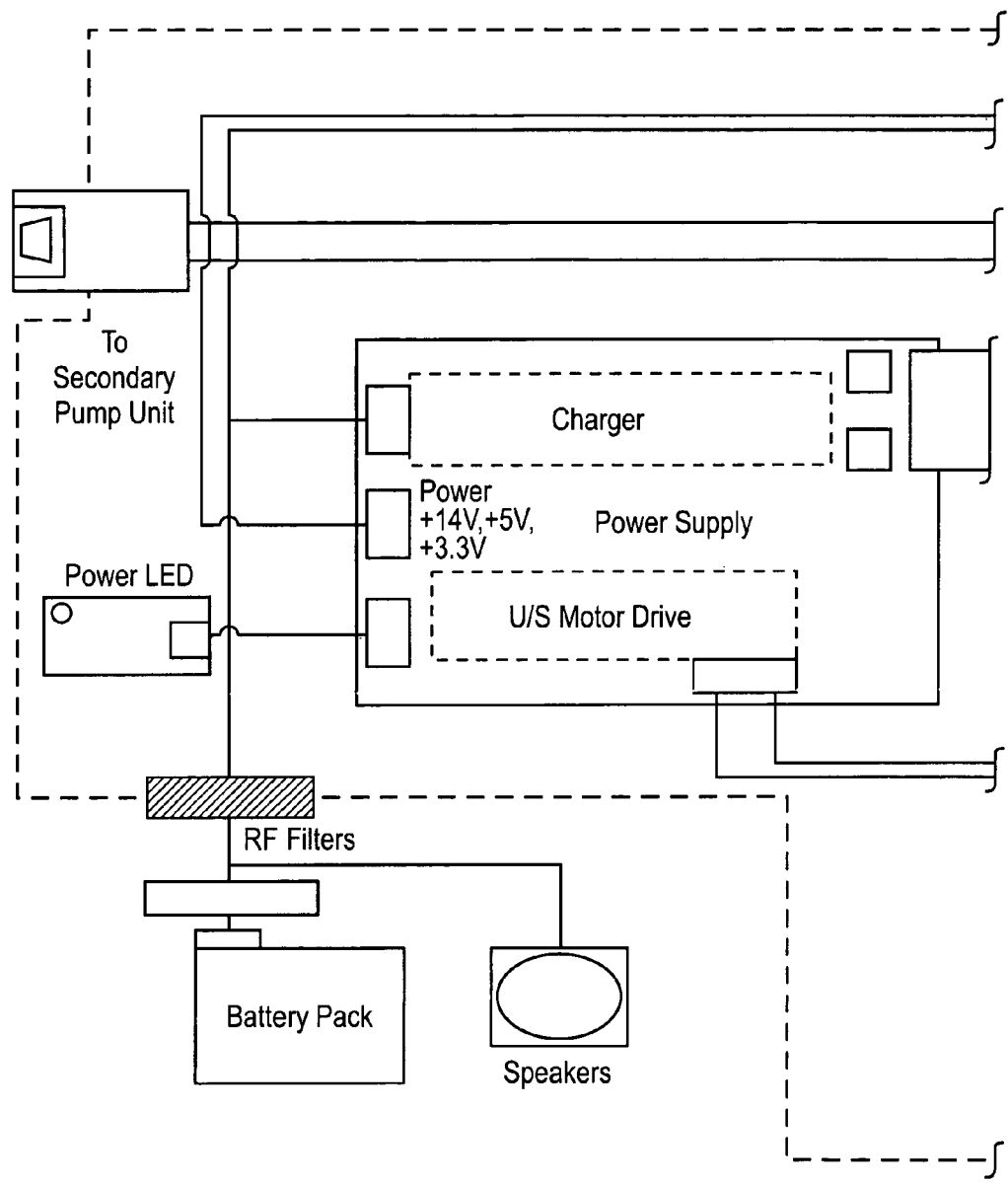
FIG. 13A  FIG. 13B →

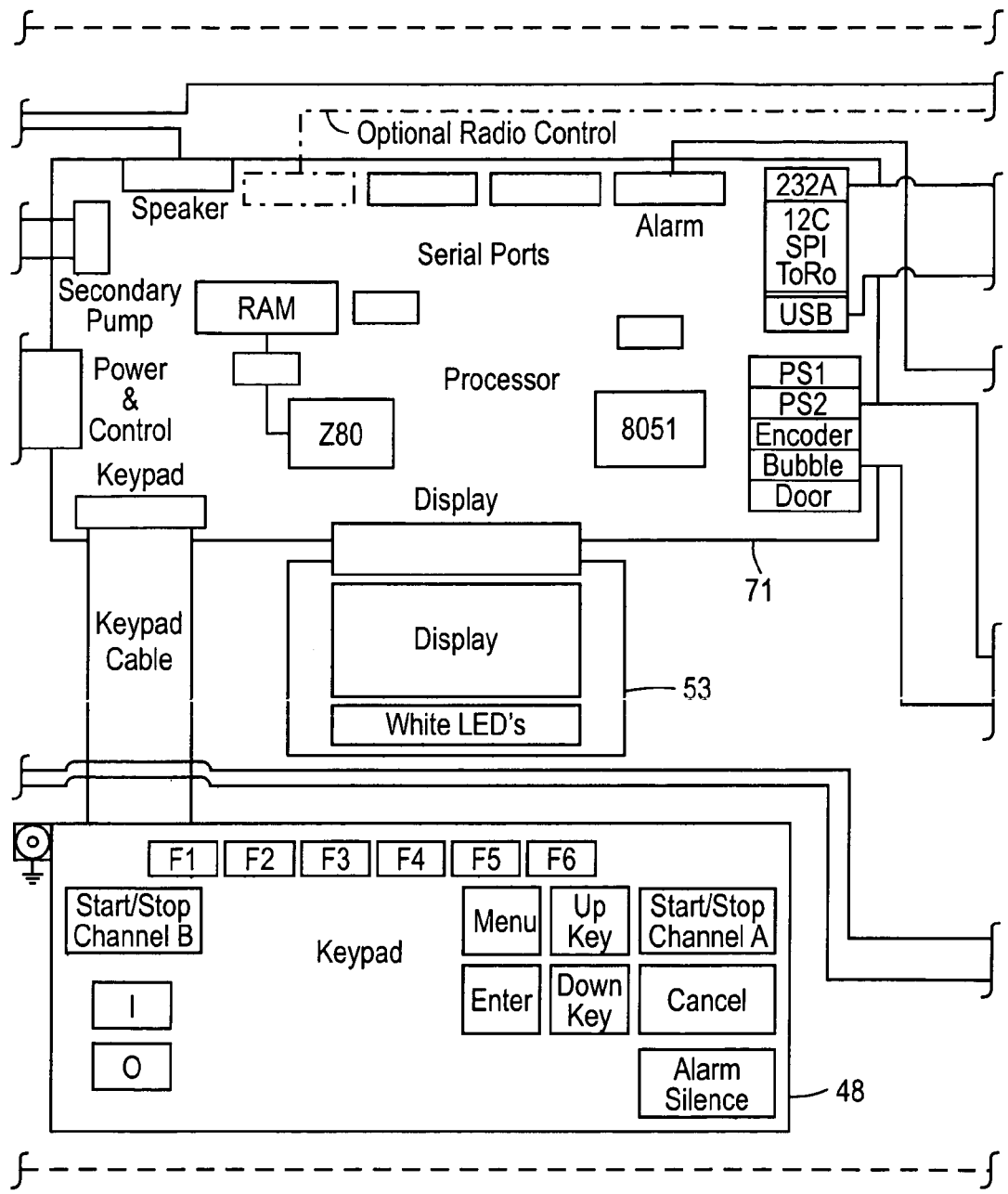
← FIG. 13A   FIG. 13B   FIG. 13C →

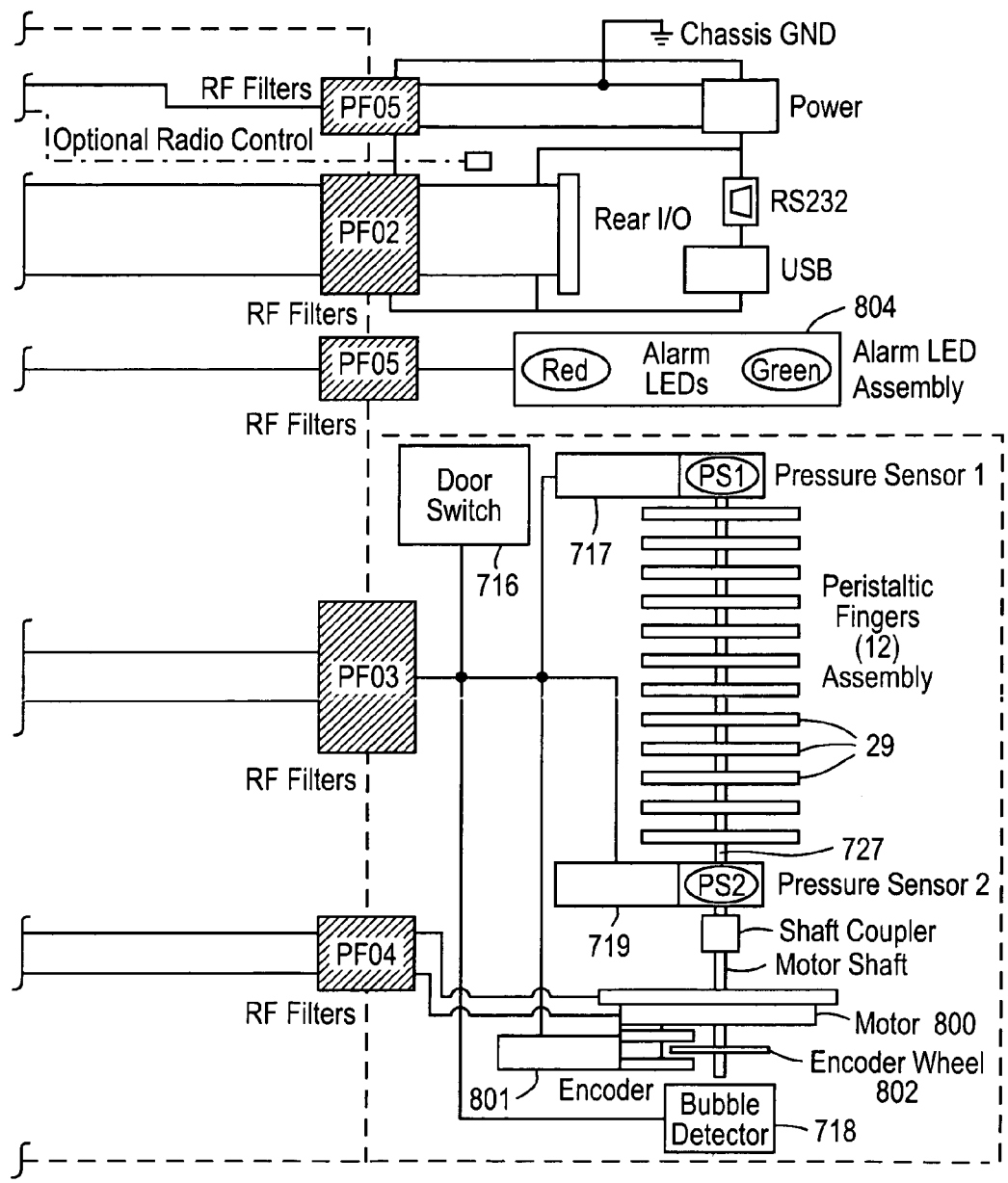
← FIG. 13B    FIG. 13C

LIQUID INFUSION APPARATUS

FIELD OF THE INVENTION

This invention relates to apparatus for refusing liquid into a patient, and more particularly to such apparatus suitable for operation in a magnetic resonance image (MRI) environment of high magnetic fields and required low radiofrequency interference.

BACKGROUND OF THE INVENTION

It is desirable to carefully control the intravenous (IV) administration of liquids to a patient. Conventional gravity IV solution delivery via commonly-available IV administration sets is typically not sufficiently accurate for the delivery of many types of fluids and drugs. Various positive displacement pumping devices have been developed for carefully controlling such IV administration. Some types of IV pumps control flow within a standard IV administration set via peristaltic (either linear or rotary) pumping schemes directly on the tubing of a conventional IV infusion set. Other types may incorporate a proprietary volumetric cassette, and still other types utilize a syringe-like device. However, there currently exists no IV controller capable of completely safe operation within a MRI suite wherein a considerable need exists for the controlled delivery of medicinal liquids. Frequently, patients scheduled for MRI examination arrive at the MRI suite with IV solutions being administered and controlled by devices which must be disconnected as the patient is moved into the suite where high magnetic fields are present and no outside RF interference can be tolerated.

The basic characteristics of an infusion pump involve the delivery of medicinal or nutritional liquids, over time, into the venous system of a living subject. Certain physical limitations regarding the delivery rate and pressure are elemental in IV liquid-infusion control. IV fluids are pumped at pressures typically in the range of 0.2 to 10 PSI. The infusion device should include detection of over-pressure and operational limits at not more than about 20 PSI. Flow ranges typical of IV pumps are from 0.1 to 2000 ml/hr. Such specifications for conventional IV infusion apparatus are quite different from the specifications for injector devices which are often used in radiologic settings, including MRI, for purposes of very rapid bolus injection of image-enhancing contrast agents. Such devices 'push' contrast agents at pressures up to 300 PSI and in very short periods of time in contrast to IV drug delivery systems. Contrast agents are solely for image enhancement and have no medicinal value in a patient and are commonly delivered using piston or syringe-type pumps that provide the requisite high fluid pressures and rapid deliveries.

The high magnetic field surrounding MRI systems can negatively affect the operation of various devices (including conventional IV control devices), especially those devices that are constructed with magnetic materials, and can seriously jeopardize a patient's safety as a result of devices utilizing magnetic materials that can be attracted at high velocity into the magnetic field of the MRI system where patient or attendant personnel are located.

Conventional devices for infusing liquids into a patient are typically small portable units often attached to an IV pole holding both the infusion device and associated liquids to be infused. Such devices utilize either stepper-type motors or simple DC motors which include magnetic materials for providing the mechanical power required to drive the pumping unit. Further, some form of electronic control unit receives the manual inputs of prescribed infusion rate settings, and controls the pumping unit to deliver the desired quantity of liquid over time. Such control unit may emit spurious radio frequency signals as a result of poor electrical design or insufficient shielding and are therefore commonly installed outside an MRI environment and outside the shielding therefor.

With the advent of MRI procedures for the imaging of internal body structures, very special requirements must be satisfied in the design of medical devices intended to be used within the MRI environment. MRI systems exploit the physical phenomenon of nuclear magnetic resonance (NMR) by which RF stimulation of atomic nuclei within an associated magnetic field results in the emission of a small RF 'spin echo' from the nucleus so stimulated. In the case of patient imaging, hydrogen nuclei bound with water are the usual targets for magnetic resonance at selected frequencies. Other molecules and compounds can also be selected for study, as in Nuclear Magnetic Spectroscopy, by choosing resonance specific magnetic field strengths and associated radio frequencies. For simplicity the typical hydrogen atom-based MRI image-acquisition process is referred to herein, but it should be recognized that the subject invention is equally useful in MRI spectrographic studies at a plurality of field strengths and frequencies.

The typical MRI system includes several components, as shown in FIG. 1. For example, the operator's console 25, 27 and various processing 37, display 29, 31 and radio frequency and magnetic gradient amplifying equipment 33, 35 are all located outside of the environment of the MRI scanning suite which must be configured to eliminate image-degrading radio frequency interference and field effects of metallic structures that can introduce field distortions and become safety hazards. The MRI scanning unit produces large magnetic and RF fields, and must be capable of receiving the extremely small RF nuclear 'echoes', and is therefore typically located within a shielded room 11. Such rooms greatly attenuate outside RF noise and may also provide some containment of the scanner's magnetic fields that include both fixed high B field and dynamic fields due to high-field ramping gradients.

However, certain devices are required to be placed in the scan room either to assist with care of the patient being imaged or for the use of attending staff. Of particular interest are those devices which must be placed in the scan room during the time of image acquisition when the patient is present and the magnetic fields are 'up' and RF reception of the tiny nuclear 'echoes' must be cleanly acquired. Electrically passive metallic items such as oxygen bottles or 'crash carts' present safety hazards to the patient due to their potential to be strongly attracted by the magnetic field of the scanner. Such items can be 'pulled' into the imaging volume where the patient is located, creating potential for serious injury or death. Additionally, great effort is made during the manufacture and installation of the scanner/magnet to assure that the lines of flux within the imaging volume are highly homogenous to assure that acquired images have minimal spatial distortion. Thus, devices formed of magnetic material that are positioned within the magnetic field of the scanner can introduce distortions into this homogeneous field and the resultant images. The level of hazard and the degree of field/image distortion due to magnetic materials depends upon the composition and location with respect to the imaging volume.

The hazards due to 'flying' objects can be controlled to some degree by the use of non-ferrous devices such as the aluminum oxygen bottle. Additionally, the gravitational weight of some devices or their rigid fixation in the scanning room may be sufficient to overcome the force of magnetic attraction on the ferrous mass of such devices toward the imaging volume. However, such devices with some ferrous mass, though inhibited from being pulled into the magnetic field, may nevertheless introduce inhomogeneity in the magnetic field. Distortions in the homogeneity of the magnetic field within the imaging volume must be kept at such a level as to be of minimal consequence to the operator reading the resultant image or data. And, the possibility of field distortion is proportionally increased as devices with metallic materials are positioned closer to the imaging volume, with the most critical position being near the center of the imaging volume, essentially where the patient is positioned. Additionally, because of the extremely low levels of RF signals produced by the target image nuclei, great care must be taken to assure that devices with active electronic circuits do not emit spurious RF signals as forms of electronic noise. Such noise can so degrade the signal-to-noise ratio of signals received by the MRI sensor coils and receivers that image resolution is reduced or rendered completely unreadable. Active circuits must be carefully shielded to assure that their RF emissions are extremely low at the specific frequencies of the imaging process. Conversely, it is possible through careful design, to place a source of RF energy for signal transmission, therapy, or the like, within the MRI environment, but such signals must be chosen to avoid the discreet Lamar frequencies unique to the particular magnetic field strength of a given MRI scanner, and must be of such high spectral purity as to coexist with the MRI without causing any deleterious effects. The intense magnetic fields produced by the MRI scanner can cause detrimental effects on the performance of common DC and stepper motors in devices needed within the MRI scanning room, to the point of making their control difficult or causing their complete failure. The gradient or time-varying magnetic fields can induce changing (AC) currents in motors and associated circuitry which may also cause false motor operation.

For example, injectors of image-enhancing contrast agents are commonly required to inject such contrast agent during actual imaging acquisition, and such devices include motors that contain magnetic material and that must therefore be located at a sufficient distance to reduce interactive effects with the magnet of the MRI scanner for proper operation and safety. Controllers and consoles of electronics and displays that generate spurious RF signals are therefore located outside the MRI scan room to avoid interference with the sensitive RF receivers of the RF scanner.

Accordingly, it is desirable to provide a self-contained, MRI-compatible infusion pump for the relatively long term control and delivery of the various infusion solutions and drugs routinely delivered to a patient within the MRI environment during image acquisition. Such devices must not emit any significant RF emissions that might adversely affect image acquisition operation from within the MRI scan room and must not interact with the magnetic fields therein either to cause distortion of the field or to be influenced by these fields sufficiently to jeopardize reliable operation of such devices.

For various reasons, including cost, safety, convenience, and performance, it may be desirable to use the MRI-compatible pump only for short durations while the patient is in the MRI. In this case, the patient must be disconnected from a non-MRI-compatible pump and connected to the MRI-safe pump prior to the MRI, and later switched back. Switching a patient's IV set involves a health risk due to sterility concerns and a cost in medical personnel's time. Additionally, fluid may be wasted from a prescribed volume during the IV-switch procedure.

Therefore, it is also desirable to provide a method for substituting an MRI-compatible pump for a prior-connected, non-MRI-compatible pump for a short duration without removing the patient from the original IV set. The MRI-compatible pump may be connected in substitution for the original pump after the original pump is removed. The original pump may be similarly reconnected, and the MRI-compatible pump removed, after the MRI is complete. By easily interchanging pumps on the same IV set installed on a patient, the time and expense of interchanging pumps are minimized, and compromises of the sterility of an IV installation on a patient are minimized.

An IV set commonly includes a length of tubing to extend from a fluid connector at a source of a liquid to be infused into a patient to a fluid connector disposed at a distal end of the tubing for connecting to an intravascular needle. It is desirable to be able to rapidly transfer a patient that is begin infused with liquid via a pump that is non-MRI compatible to a pump that is MRI compatible in preparation of the patent for MRI procedures, without disconnecting the tubing or removing the needle from its intravascular function, or other actions which may compromise sterility or inconvenience the patient.

SUMMARY OF THE INVENTION

In accordance with the illustrated embodiment of the present invention a safe and effective infusion device for use within the MRI scan room achieves reduction of magnetic material and accurate pumping control as well as reduction of RF emissions. In one embodiment, the infusion device includes an ultrasonic motor that eliminates magnetic materials and that does not produce any detrimental magnetic fields and that is not affected by external magnetic fields. The ultrasonic (U/S) motor drives a peristaltic or other suitable fluid pumping mechanism, and is driven by a multiphasic electronic signal specifically designed to produce very little RF harmonic noise in the spectral range of about 6 or 8 MHz to about 130 MHz in which MRI receivers are most sensitive. The drive power for the U/S motor is generated via circuitry which produces multiphasic drive signals of at least sine and cosine wareforms at related ultrasonic frequencies. These drive signals are produced as a sinusoidal wave to reduce high frequency harmonic components which may disturb the MRI's RF-sensitive responsiveness. One scheme for producing these multiphasic signals uses coreless or "Air Core" transformers constructed with inherent leakage inductance that interacts with the complex impedance of the U/S motor to convert lower voltage square wave signals at the primary winding into sinusoidal high voltage signals at the secondary windings suitable for powering the U/S motor and producing little harmonic RF interference. Alternatively, D.C. voltages of opposite polarities can be alternately switched to supply alternating voltages. The switched signals can be filtered into sinusoidal signals and applied to the inputs of high voltage linear amplifiers that are set for such gain as needed to produce resultant outputs of sufficient voltage and sinusoidal shape to drive the U/S motor.

Control electronics receive commands through an input keypad for setting prescribed fluid flow rates to be delivered, and such inputs are translated into signals to control the U/S motor and pumping mechanism. Various safety devices feed back operational information to the control electronics, including detection of motor speed and motion of pump elements, air bubbles in the fluid path, drip rate, high pressure, low fluid, low/no flow, overtime, and the like. The present infusion device includes battery power for portability, and is housed in one RF-shielded, non-magnetic housing for convenient location anywhere within the MRI scan room without introducing image degrading RF interference or producing distortions of the homogeneous magnetic field, and without being affected by the strong magnetic fields or RF energy produced by the MRI system. Such unrestricted placement of the device is of great importance to the safety and convenience of the attending MRI staff and imaging patient. Further, in the case of a linear peristaltic pump mechanism, the particular position of pump elements, along with the speed of motion of these elements, must be known to the controller. The degree to which the controller may modulate speed and control exact positions of the pump elements directly affects the resolution and accuracy of the fluid delivery system. To provide a high degree of speed and position accuracy, an optical encoder (801, 802) is installed along the main pump shaft. The encoder disk (802) has many small graticule marks about the circumference, and a single index mark. The optical sensor (801) detects the marks and produces output signals indicative of both the index and individual graticule marks. The index occurs only once each 360 degrees of rotation to facilitate the controller sensing an index to know the position of the pumping elements. The rate at which the graticule marks are sensed indicates the speed of the pump shaft as well as its fine position relative to the index mark. The controller responds to the optical encoder to modulate the speed of motion of the pump elements at specific positions of the pump shaft in order to reduce inherent non-linearities in fluid delivery of the linear-type peristaltic pump. In this way, highly accurate and linear fluid flow may be achieved.

In an additional embodiment, a method is employed to substitute an MRI-compatible pumping device for a prior-connected, non-MRI-compatible pumping device while preserving the patient's connection to a prior-connected primary intravenous (IV) infusion set. The patient is commonly connected to a primary IV set through a primary, non-MRI-compatible pump. Upon arrival at the MRI suite, a secondary, MRI-compatible pump attached to a secondary IV set connects to the primary IV set to continue actively-pumped IV fluid delivery. The primary pump is disengaged from the patient's installed primary IV set, and a flow preventer (to shut off flow) that is standard on most IV sets is activated to inhibit liquid flow through a segment of the primary IV set. The fluid-receiving or proximal end of the secondary IV set is connected to the upstream end of the primary IV set near the source of the IV fluid. The upstream connection may be conveniently formed by puncturing a conventional "Y" connector on the primary IV set with a hollow needle on the secondary IV set, or via a luer-type "Y" site connector. Air is flushed from the secondary IV set by flowing fluid from the upstream connection, and the fluid-delivery or distal end of the secondary IV set is then connected in similar manner at a downstream connection in the primary IV set. Pumping of the liquid may then be resumed using the MRI-compatible pump operating on the secondary IV set without having dislodged the intra-vascular needle or actually opening the primary IV circuit. The patient and MRI-compatible pump may then be moved close to the MRI scanner while maintaining the controlled IV therapy. The secondary IV set so employed may simply be disconnected and discarded after the MRI procedure, again without opening the original primary IV circuit, and the original primary IV set may be reinstalled into the original, non-MRI-compatible pump while preserving the patient's connection to the primary IV set. By not opening the fluid circuit of the primary set, minimal risk to the patient and sterile IV path are achieved as well as reducing medical waste and cost of replacing the primary IV set after the MRI procedure.

To facilitate rapid transitions between primary and secondary pumps and infusion sets, one embodiment of the present invention includes an infusion device that receives a liquid conduit for delivering liquid to a patient at volumetric rates that are controllable by the device. Peristaltic pumping of liquid through the conduit installed within the device is enabled only upon proper registration of a flow valve within a receptacle of the device for actuation upon closing of a safety door. Flow of liquid through the conduit is inhibited upon opening the safety door, and various sensors are incorporated into the device along the path of the conduit to detect inflow and outflow liquid pressures, available liquid supply, air bubbles in the conduit, and the like.

BRIEF DESCRIPTION OF THE DRAWINGS

FIGS. 13A, 13B and 13C comprise a block schematic diagram illustrating operating components of the illustrated embodiment of the present invention;

DETAILED DESCRIPTION OF THE INVENTION

Figure 1:
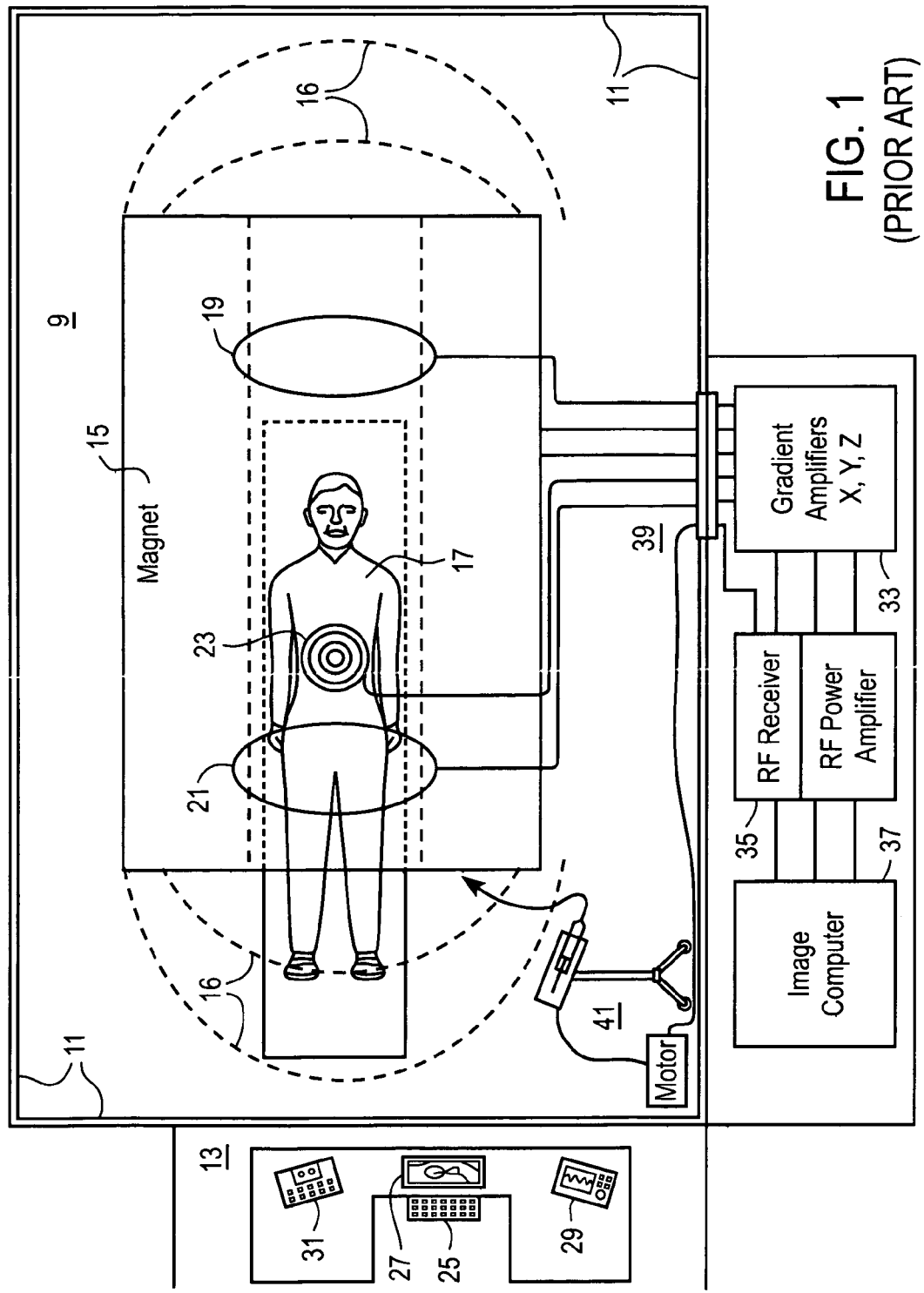
FIG. 1 is a pictorial plan view of a conventional MRI system showing typical placement of operational components.

Pending application Ser. No. 10/964,333 entitled "Non-Magnetic Medical Infusion Device", filed on Oct. 12, 2004 by R. Susi, and issued U.S. Pat. No. 7,267,661 entitled "Non-Magnetic Medical Infusion Device" filed on Jun. 17, 2002 by R. Susi are incorporated herein in their entireties by this reference thereto. Referring now to the plan view in FIG. 1 of an MRI system, the scanning room 9 is disposed within shielding boundary walls 11, with a control room 13 for operators or attendant personnel positioned outside the boundaries of the scanning room 9. The scanning room 9 includes the image acquisition equipment including a source 15 of intense magnetic field 16 that emanates from the source in substantially homogenous array throughout the adjacent space and around a patient 17. Various components of the system for performing the image acquisition operations, including gradient 19 and sensor 21 and RF coils 23 are disposed about the patient 17 for stimulating the nuclei 'echos' to map the positions thereof within the spatially-homogenous magnetic field 16 as the patient's body is scanned in conventional manner along multiple orthogonal axes. The shielding boundary walls 11 (and ceiling and floor) provide shielding against radio-frequency interference and, as fabricated with ferrous materials, may also establish outer limits of the magnetic field distribution around magnetic source 15.

The control room 13 is disposed outside the shielding boundary walls 11 and is equipped with computer input keyboard 25, computer display 27, monitor 29 of patient's vital life signs, controls 31 for liquid infusion apparatus, and the like. Such representative equipment is housed outside the shielding boundary walls 11 to inhibit intrusion of spurious magnetic and electrostatic and RF signals into the image acquisition operations within the scanning room 9. Similarly, the gradient amplifiers 33 for amplifying signals from conventional gradient coils 19-21, along X, Y, and Z coordinates and RF amplifiers 35 and the image-processing computer 37 are also located outside the shielding boundary walls 11 for the same reason. The thru-wall interconnections 39 between the components within the scanning room 9 and the electronic equipment 25, 27, 29, 31, 33, 35, 37 disposed outside the room 9 typically also includes RF filtering to diminish the sources and the portals by which and through which RFI signals may enter the scanning room 9.

A high-pressure liquid-injection device 41 commonly resides within the scanning room 9 to administer IV injection into the patient 17 of liquid compositions, for example, that enhance image acquisition (e.g., contrast medium) or that otherwise provide diagnostic or therapeutic benefits to the patient 17 being scanned. Such conventional injection device 41 should desirably be positioned close to the patient 17 to facilitate IV liquid infusion, but must be positioned remotely to avoid disrupting the homogeneous magnetic field 16, and to minimize RFI and operational failures of the infusion device 41 resulting from operating in the intense magnetic field adjacent the patient 17. Control of such infusion device 41 may be via remote controller 31 disposed within control room 13.

Figure 2:
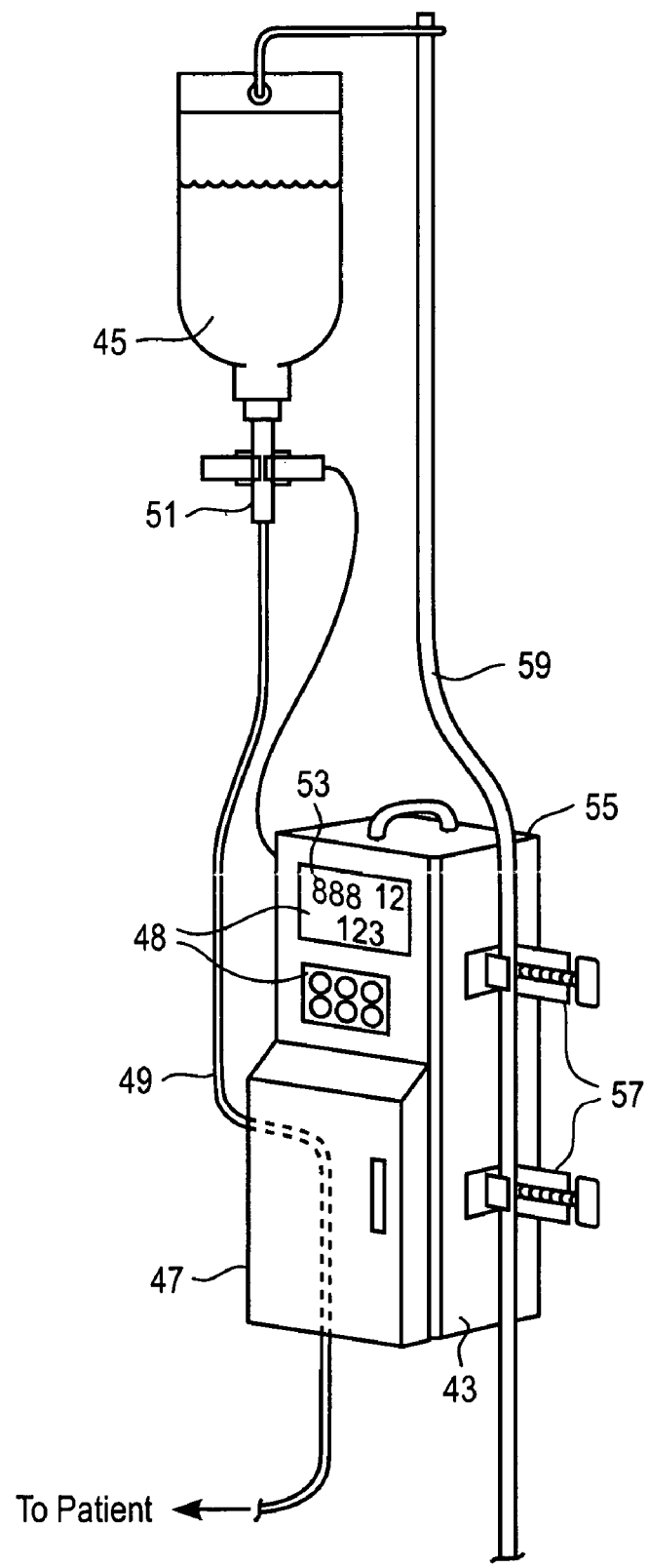
FIG. 2 is a partial perspective view of an infusion device in accordance with one embodiment of the present invention.

In accordance with the embodiment of the invention illustrated in FIG. 2, an improved liquid infusion device 43 is operable within intense magnetic fields and with negligible RFI to provide positive displacement of a liquid 45 such as saline or antibiotics, or sedative, or the like, in controlled volumes per unit time. The device does not include any ferrous or magnetic materials, and is substantially shielded against irradiating any RFI during operation. Specifically, the device 43 includes a pump in the lower chamber 47, as later described herein. The pump chamber 47 receives therein the flexible, resilient tubing 49 that is pre-packaged and sterilized as a component of a conventional IV liquid infusion set that also includes a conventional drip chamber 51 as part of the infusion set. Controls for the pump in chamber 47 include an operator's input keypad 48 that is shielded against radiation of RFI for setting infusion parameters, and a drip detector 53 that may be disposed about the drip chamber 51 to detect flow of liquid from the supply 45. A display 53 is positioned in the upper portion of the housing 55 which may be formed of non-magnetic, RF-shielding material such as conductively-coated plastic or aluminum, or the like. The housing 55 attaches with one or more clamps 57 to a rigid support 59 formed of non-magnetic material such as fiberglass or aluminum, or the like.

Figure 3:
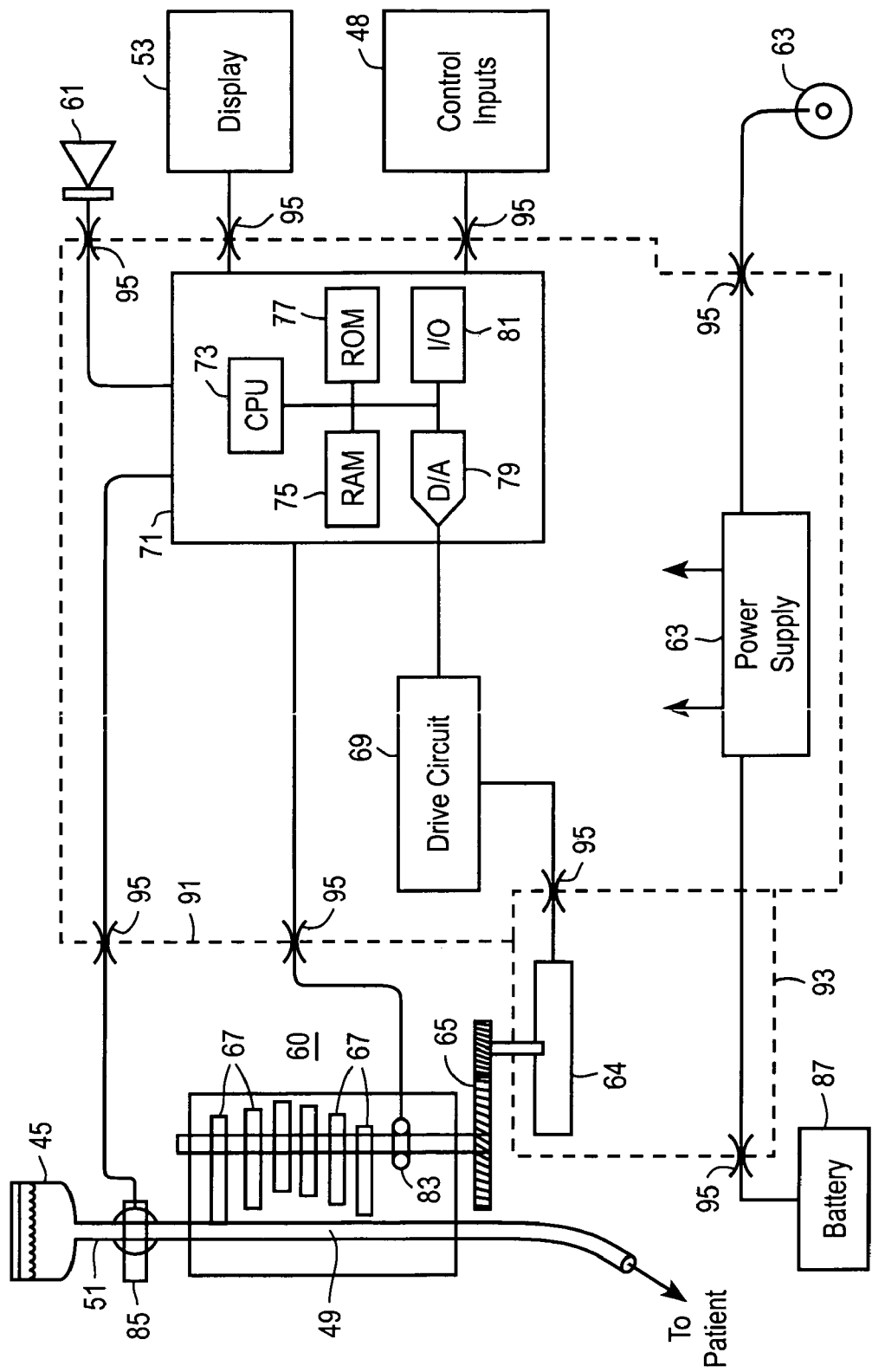
FIG. 3 is a block schematic diagram of the infusion device of FIG. 2.

Referring now to the pictorial block schematic diagram of FIG. 3, there is shown a peristaltic-type positive-displacement pump 60 disposed within the pump chamber 47 of the housing 55 to operate with the length of tubing 49 that passes therethrough between the drip chamber 51 and the patient. The peristaltic pump 60 (linear or rotational) is driven by an ultrasonic motor 64 via appropriate mechanical linkage 65 to actuate a squeeze roller against the tubing 49 in known peristaltic pumping manner, or to actuate a series of elements 67 through a linear tubing-squeezing sequence to produce peristaltic pumping action in known manner. Various visual and audible annunciators 61 may be provided to signal operational conditions either within acceptable limits, or within error or failure conditions.

A conventional ultrasonic (U/S) driving motor 64 is powered in known manner by multiphasic signals applied thereto from the motor drive circuit 69. A controller 71 for the device includes a central processing unit 73 with associated peripheral components including Random Access Memory (RAM) 75, Read-Only Memory (ROM) 77, Digital-to-Analog (D/A) converter 79, and an Input/Output channel 81. This controller 71 receives input control information from the operator's keypad 48, and receives feedback information about pump speed from sensor 83 and about liquid flow from drip detector 85 disposed about the drip chamber 51. In response to the inputs supplied thereto, the controller 71 operates on stored programs to actuate a display 53 of operating parameters (or other data), and to actuate the motor drive circuit 69 for energizing the ultrasonic motor 64 for rotation at a controlled speed. A power supply 63 is connected to the controller 71 and drive circuit 69 to supply electrical power thereto, and is connected to a battery 87 to receive electrical power therefrom during stand-alone operation, or to receive line voltage via plug 63, as required.

In accordance with this embodiment of the present invention, no magnetic material is used in any of the components of the infusion device 43 including the ultrasonic motor 64, pump 60, power supply 63, controller 71 and associated components. Additionally, none of such components is adversely affected during operation by a strong magnetic field. And, any RF energy that may be generated by electronic signals within the ultrasonic motor 64, drive circuit 69, controller 71, power supply 63 or associated components is specifically shielded by conductive structures 91, 93 disposed around such components to inhibit radiation of RFI. Additionally, radio-frequency interference filters 95 are disposed about all through-shield conductors to inhibit radiation of RFI through such portals.

Figure 4:
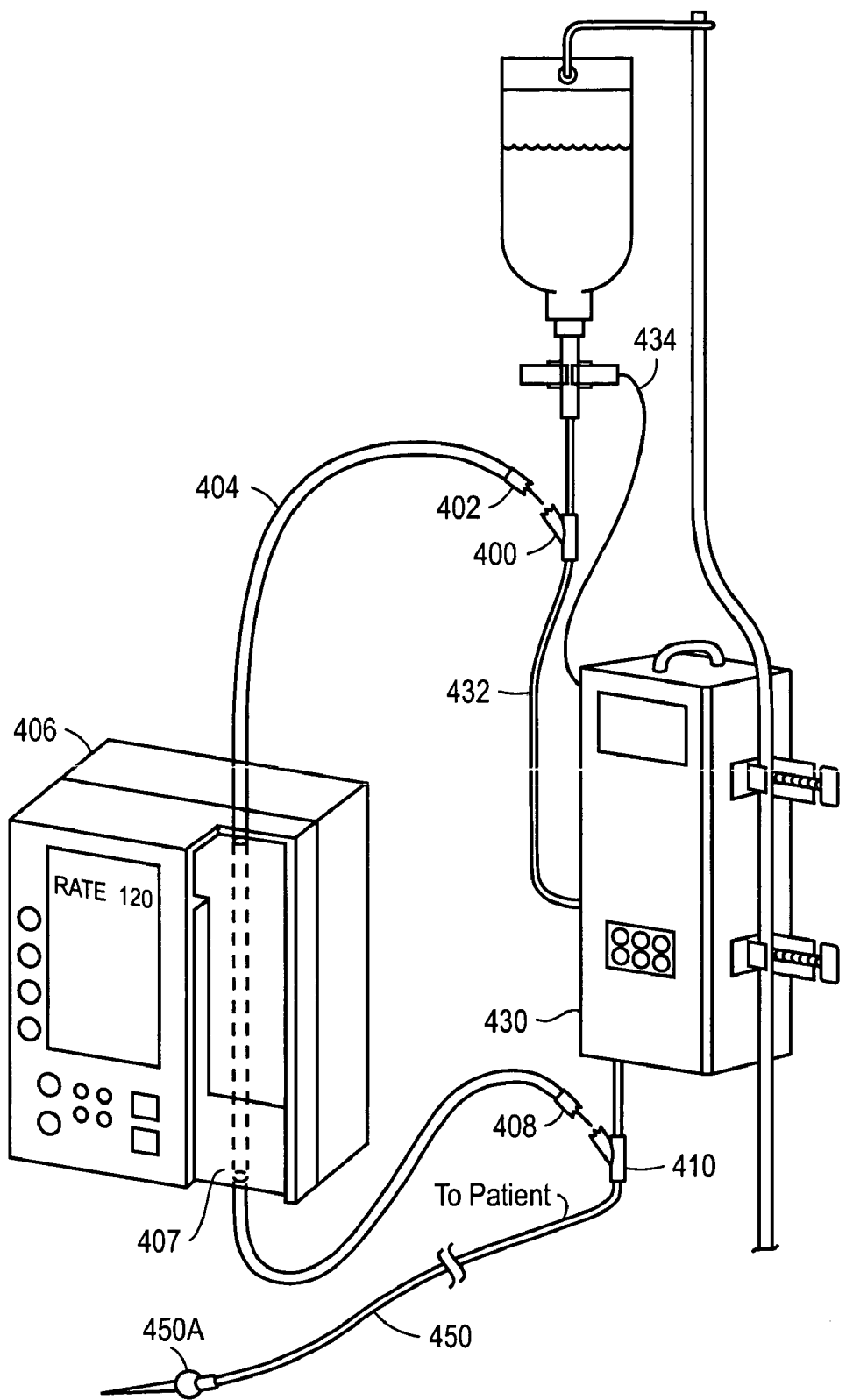
FIG. 4 is a partial perspective view of the two pumping apparatuses in accordance with one embodiment of the present pump-substitution invention.

Referring now to FIG. 4, in an additional embodiment of the present invention, a method is employed to substitute an MRI-compatible pumping device 406 for a prior-connected, non-MRI-compatible pumping device 430 while preserving the patient's 450 connection to a prior-connected primary IV infusion set 432. The patient is initially connected 450 to the primary IV infusion set 432 which is installed in a non-MRI-compatible primary pump 430. The primary pump 430 controls the pumping action in response to information entered into the unit, and in response to a sensor 434 that monitors liquid flow. Fluid connectors are disposed in the primary IV set upstream 400 and downstream 410 of the primary pump 430. Compatible fluid connectors are also disposed in the secondary IV set upstream 402 and downstream 408 of the secondary pump 406.

Figure 5:
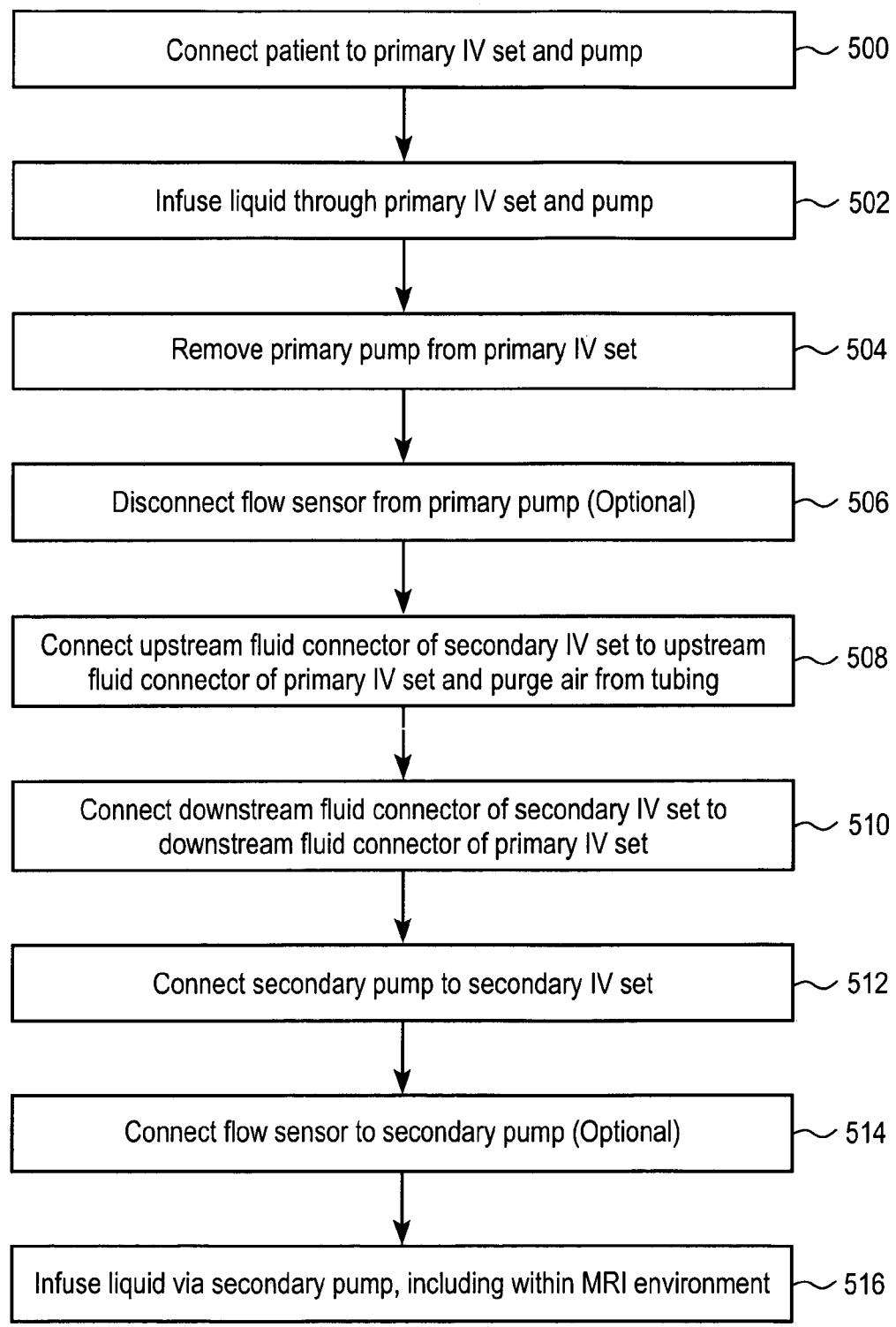
FIG. 5 is a flowchart illustrating a method of temporarily substituting a secondary IV pump for a primary IV pump without removing the patient's primary IV set in accordance with the present invention.

Referring now to the flowchart of FIG. 5, a method is illustrated for substituting an MRI-compatible pumping device 406 for a prior-connected, non-MRI-compatible pumping device 430 while preserving the connection 450 of a prior-connected primary IV infusion set 432 to a patient. Initially, the patient is connected 500 to the primary IV set 432 and primary pump 430, and liquid is infused 502 into the patient through the primary IV set 432 and primary pump 430. Before entry of the patient into the MRI environment, the primary pump 430 is disabled from pumping liquid, and the flow of liquid through the primary IV set 432 is inhibited via a shut-off mechanism within the primary IV set.

The secondary MRI-compatible pump 406 is configured to operatively receive a secondary IV set 404. The secondary pump 406 may include a sensor for monitoring liquid flow to control the pumping action.

To transition a patient from a non-MRI-compatible pump 430 to an MRI-compatible pump 406 without altering the primary IV set 432 as installed on a patient, the upstream fluid connector 402 of the secondary IV set 404 is connected 510 to the upstream fluid connector 400 of the primary IV set 432. After purging the tubing of air, the downstream fluid connector 408 of the secondary IV set 404 is connected 512 to the downstream fluid connector 410 of the primary IV set 432. The secondary IV set is operatively installed 508 into the secondary MRI-comptabile IV pump 406. In one embodiment, a sensor 434 may be connected 514 to the pump 406 for measuring the liquid pumped from the liquid source. Liquid is infused 516 into the patient through the connection 450A of the primary IV set 432 to the patient, and through the secondary IV set 404 and secondary pump 406. Because the secondary pump 406 is MRI-compatible, the infusion may continue via the secondary pump 406 within the MRI environment. The primary IV set 432 remains installed on a patient who therefore does not have to be directly connected at 450A to the secondary IV set 404, but rather the secondary IV set 404 "bypasses" the section of the primary IV set 432 that remains occluded between connectors 400, 410.

In an additional embodiment, the secondary pump 406 is connected to the primary IV set 432 before the primary pump 430 is operatively disengaged and removed from the primary IV set 432.

Figure 6:
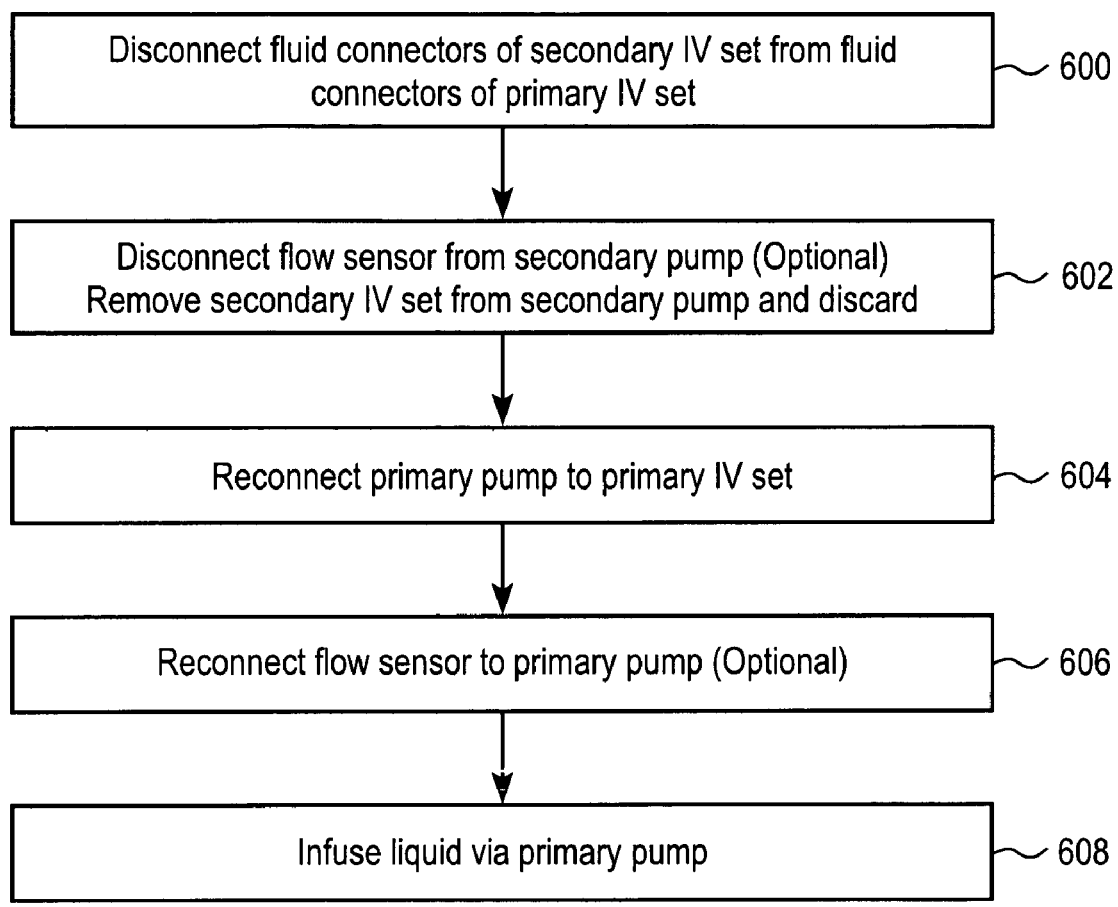
FIG. 6 is a flowchart illustrating a method of replacing a secondary IV pump with a primary pump in accordance with the present invention.

Referring now to the flowchart of FIG. 6, a method is illustrated for removing the secondary pump 406 and reconnecting the primary pump 430 after the patient is removed from the MRI environment. The fluid connectors 402 and 408 of the secondary IV set 404 are disconnected 600 from the fluid connectors 400 and 410 of the primary IV set 432. This prevents flow of liquid through the secondary IV set 404. In one embodiment, the flow through the primary IV set 432 is prevented by a shut-off mechanism disposed in the primary IV set 432 between connectors 400 and 410. Such shut-off mechanism may manually cut off fluid via hand-operated slide or roller clamp, or the like. The secondary IV set 404 is operatively re-installed removed 602 from the secondary pump 406 and is discarded. The primary pump 430 is operatively re-installed on the primary IV set 432 to which the patient remains connected 450. The flow sensor 434 may be reconnected to control the rate of liquid infusion through the primary IV set 432. Liquid is again infused 608 into the patient via the primary IV set 432, the primary pump 430 and the original connection 450 of the primary IV set to the patient.

Figure 7:
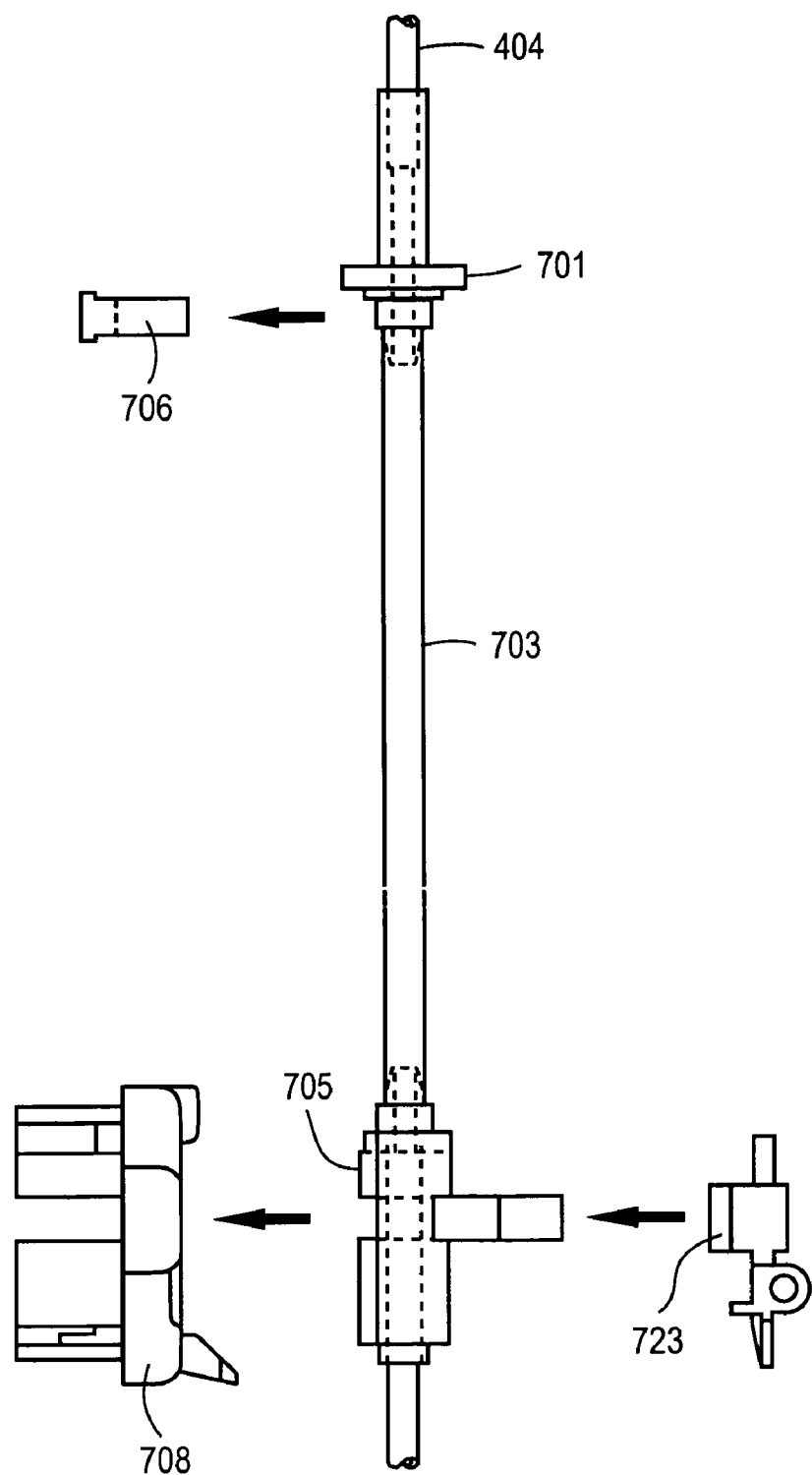
FIG. 7 is a side view of a length of precision tubing in accordance with the present invention.

Referring now to FIGS. 4 and 7, there are shown perspective and side views, respectively, of operational aspects of the liquid-delivery systems in accordance with one embodiment of the present invention. Specifically, a liquid conduit 404 includes a fluid connector 402 at an input or proximal end, and includes a flanged connector 701 that couples the proximal segment of the liquid conduit 404 to an intermediate segment including a length of precision tubing 703, as later described herein, that terminates in flow valve 705. A distal segment of the fluid conduit includes a fluid connector 408 at the distal end thereof, and is coupled at its proximal end to the flow valve 705. The entire assembly including proximal and distal segments of the fluid conduit 404, fluid connectors 402, 408, flanged connector 701, precision tubing 703 and flow valve 705 is prepared and sterilized and packaged in an hermetically-sealed envelope in a conventional manner for immediate installation in the pumping device 406, as needed to infuse liquid into a patient conveniently during an MRI procedure.

The precision tubing 703 may be formed as a thin-walled extrusion of a flexible, elastic material such as silicone rubber, or other biocompatible polymer that confines a selected liquid volume per unit length within the bore of selected cross-sectional dimension between the flanged connector 701 and the flow valve 705. In this way, progressive peristaltic pumping by successive pinching and advancing of the pinch point along the tubing 703 toward the flow valve 705 administers a known volume of liquid to a patient. The length of tubing 703 between flanged coupling 701 and flow valve 705 may be slightly stretched into position within the pumping device 406 to provide resilient engagement of the flanged connector 701 and flow valve 705 within their respective mating receptacles 706, 708 disposed at opposite ends of the active peristaltic pumping mechanism of the device 406.

Figure 8:
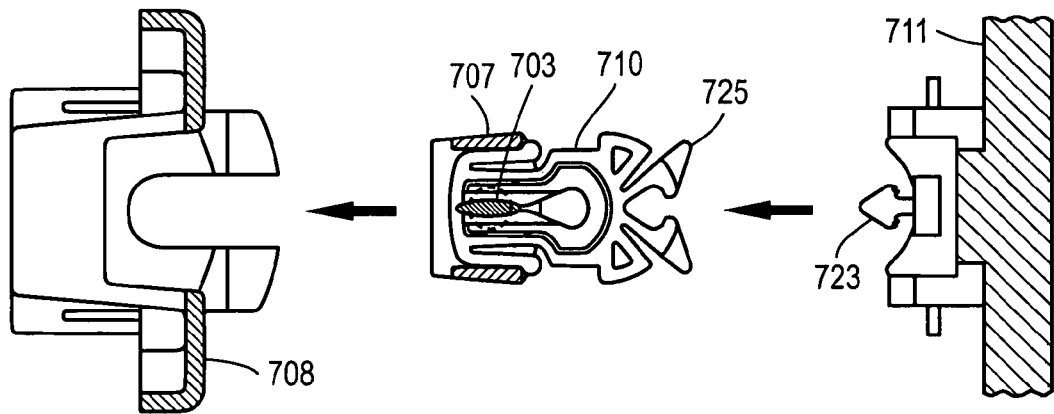
FIG. 8 is an exploded top view of valve apparatus in accordance with one embodiment of the present invention.

The flow valve 705, as illustrated in the exploded top view of FIG. 8, includes an outer housing 707 within which the precision tubing 703 passes. The mating receptacle 708 in the pumping device 406 for the housing 707 includes a complementary recess that receives the housing 707 in only one orientation and secures the properly-installed housing in place with the aid of slight tension exerted thereon by tubing 703. A slide or shuttle element 710 is disposed within the housing 707 to slide laterally relative to the elongated axis of the tubing 703, with the tubing 703 passing through a tapered aperture in the shuttle element 710. Thus, with the shuttle element 710 fully depressed within the housing 707, the tubing 703 passes through the portion of the aperture of maximum cross sectional dimension, leaving the bore of the tubing 703 fully open for unimpeded flow of liquid therethrough. In alternate position of the shuttle element 710 maximally protruding from the housing 707, the tubing 703 is pinched within a portion of minimal cross-sectional dimension of the aperture, as shown, to inhibit liquid flow through the tubing 703. Thus, as initially installed within the pumping device 406, the flow valve 705 is configured to inhibit flow through the liquid conduit 404 to ensure no inadvertent dosing of a patient until the pumping device 406 is rendered fully operational.

In accordance with one embodiment of the present invention, the device 406 is inhibited from administering liquid to a patient until a liquid conduit 404 is properly installed and an access door 407 is fully closed and safely latched shut. The access door 407 carries passive components of interlocking elements that properly engage and interface with active components of the device 406 for proper operation only with the access door 407 fully closed and safely latched shut. The region of the device 406 that is accessed through the opened access door 407 includes a generally vertical channel for receiving the flanged connector 701 in a complementary receptacle 706 that is positioned above the peristaltic pumping mechanism 712. A sensor may be disposed above the receptacle for the flanged connector to optically sense presence of liquid in the proximal portion of the conduit 404, and operate to inhibit the pumping device 406 from further pumping activity in response to sensing an empty conduit.

The access door 407 carries an upper platen 716 that cooperates with a pressure sensor 717 disposed behind a flexible membrane 711 and intermediate the receptacle 706 for the flanged connector 701 and the peristaltic pumping mechanism 712 to position an initial length of installed tubing 703 between spaced platen 716 and pressure sensor 717. In this way, the pressure at which liquid is supplied to the device can be tonometrically determined within the precision tubing 703, or otherwise measured, for use in correcting calculation of pumping activity required to deliver a selected volumetric infusion rate of liquid to a patient.

Similarly, a platen 718 is carried on the access door 407 at a location aligned with another pressure sensor 719 disposed intermediate the pumping mechanism 712 and the flow valve 705. In the manner, similar to operation of pressure sensor 717, the pressure sensor 719 and platen 718 confine the precision tubing 703 to provide tonometric measurement, or other measurement, of outlet pressure. An upper limit of outlet pressure may be selected to trigger an alarm condition if such liquid outlet pressure exceeds the set limit as an indication of a clogged outlet conduit.

The access door 407 also carries a platen 721 positioned in alignment with the peristaltic pumping mechanism 712 to confine the precision tubing 703 therebetween to effect linear peristaltic pumping activity in the generally downward direction from inlet pressure sensor 717 toward outlet pressure sensor 719. Neither pressure sensing nor pumping activity may proceed until the access door 407 is fully closed to position the associated platens about the precision tubing 703 for proper sensing and pumping operations.

Figure 9:
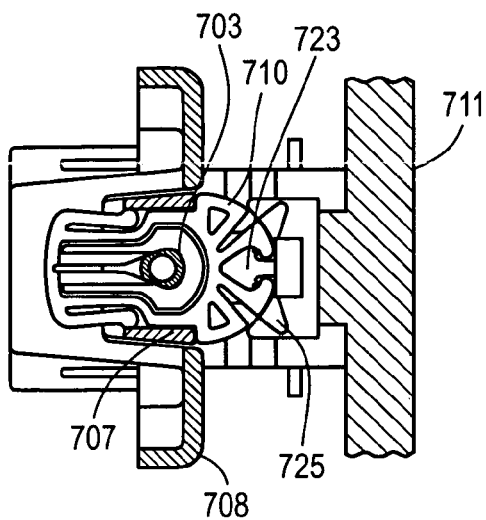
FIG. 9 is a top view of the valve apparatus of FIG. 8 in one operating configuration.
Figure 10:
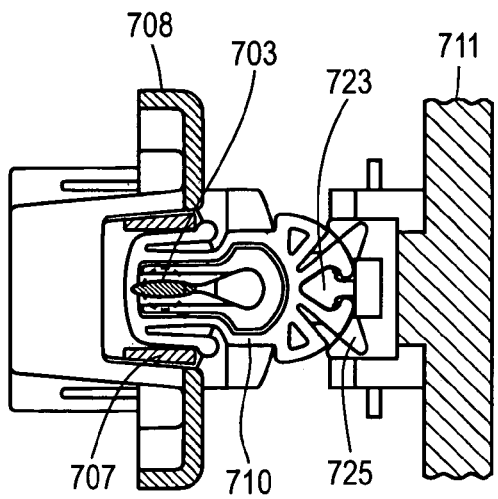
FIG. 10 is a top view of the valve apparatus of FIG. 8 in another operating configuration.

The access door 407 also carries a detent element 723 that mates with a resilient clamp 725 carried on the shuttle element 710 of flow valve 705. Specifically, these mating elements effect sliding movement of the shuttle element 710 from initially protruding position (i.e., tubing 703 pinched) toward fully open position (i.e., tubing 703 not pinched) as the access door is closed, as illustrated in FIG. 9. Additionally, the engaged detent element 723 and resilient clamp 725 remain engaged as the access door 407 is initially opened, thereby to pull the shuttle element 710 toward maximum protrusion from the housing 707 to pinch tubing 703 and inhibit further liquid flow therethrough, as illustrated in FIG. 10. The attachment of the resilient clamp 725 carried on the shuttle element 710 of flow valve 705, and the detent element 723 carried on the access door 407 is overridden and resiliently released following maximum protrusion of the shuttle element 710 and further opening of the access door 407. Of course, detent element 723 may be carried on the shuttle element 710, and a resilient clamp 725 may be carried on the access door 407 to effect similar interaction and safety operation.

An ultrasonic or optical sensor may be disposed within the device 406 at a location thereon below the flow valve 705 and about the distal segment of the liquid conduit 404 to detect the presence of air bubbles in the outlet conduit (that is formed of ultrasonically or optically-transmissive material). This sensor may include a protruding U-shaped receptacle for receiving the conduit therein and for supporting optical elements in the protruding arms of the receptacle to sense bubbles in liquid passing therebetween in the outlet flow of liquid within the conduit. A mating U-shaped element 407 is supported on the access door 711 in alignment with the U-shaped receptacle of the bubble detector to capture the liquid conduit 404 fully recessed therein in order to fully close the access door 407.

Figure 11:
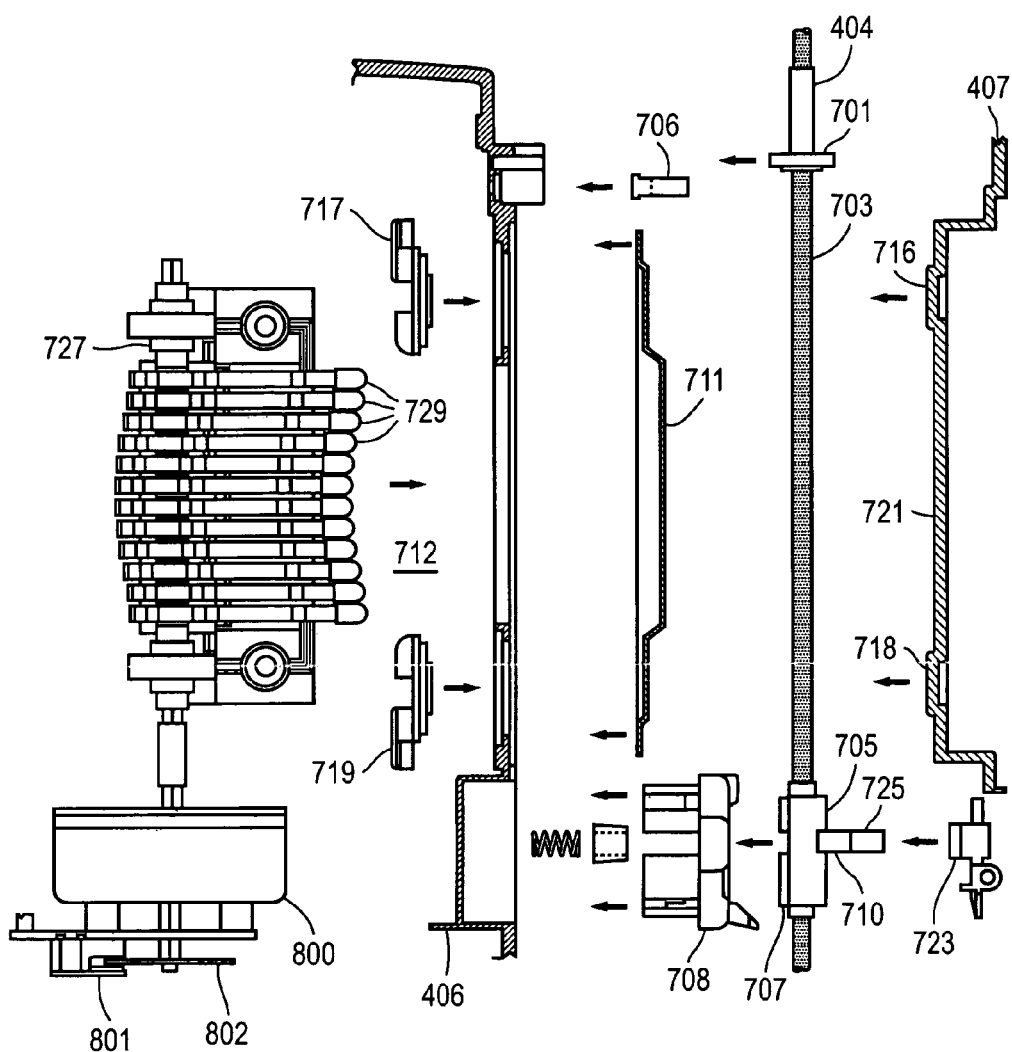
FIG. 11 is an exploded side view of operative components in one embodiment of the present invention.
Figure 12:
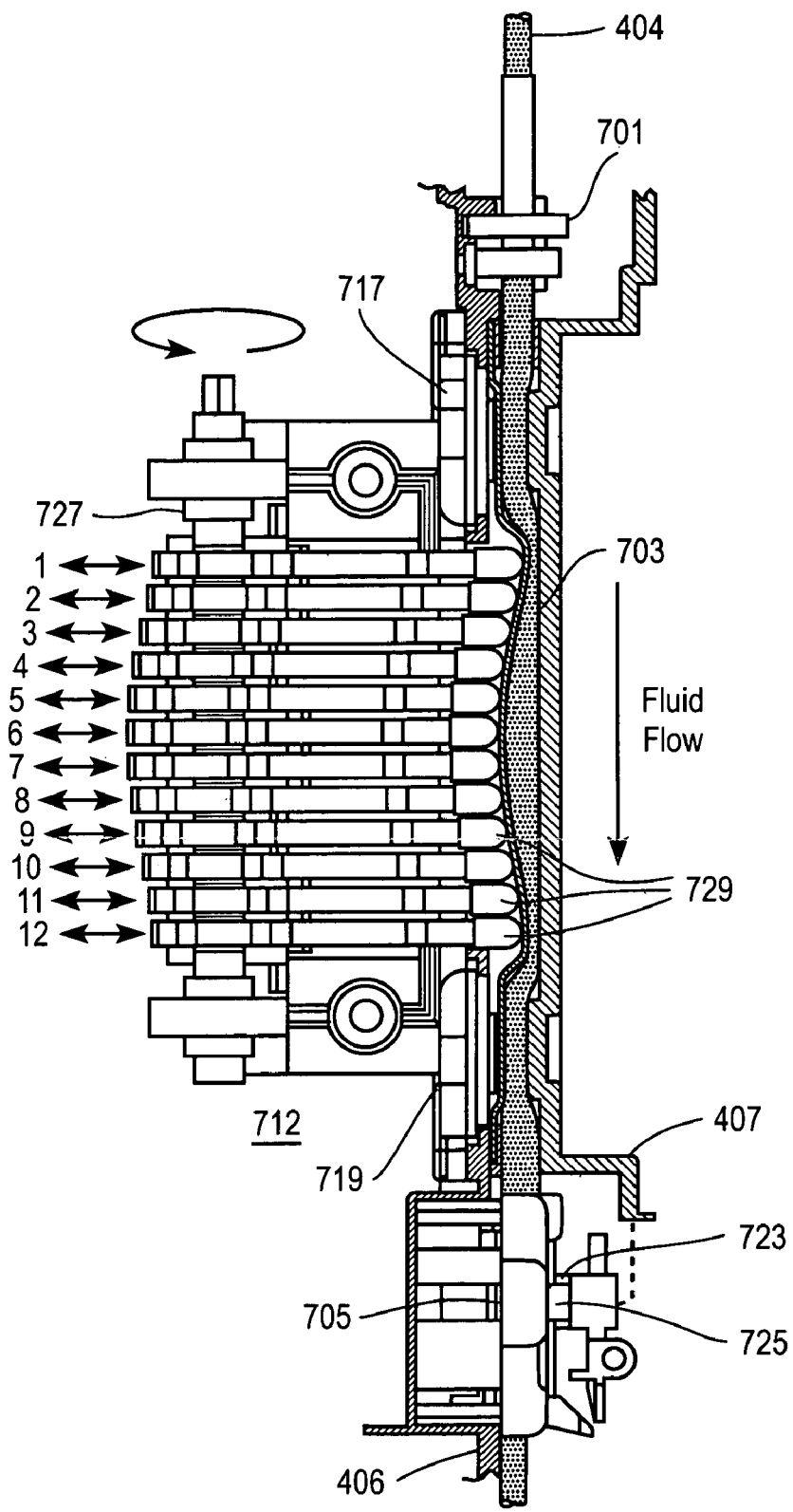
FIG. 12 is a partial side view of the embodiment of FIG. 11 in assembled, operational configuration.

Referring to the partial side view of FIG. 12, there is shown a partial side view of the components of FIG. 11 assembled into operational configuration. Specifically, the access door 407 disposed in closed configuration positions the platens 716, 718, 721 on one side of the intermediate length of precision tubing 703 against the respective sensors 717, 719 and pumping mechanism 712. The flow valve 705 is configured to open condition and liquid is pumped through the conduit 404, 703 in response to rotation of the cam shaft 727 of the peristaltic pumping device 712. In this manner, pinch points along the precision tubing 703 progress downwardly as successive pump elements 729 of the pumping device 712 are manipulated by the rotating cam shaft 727 to provide the peristaltic pumping action in known manner.

Referring now to FIGS. 13A, 13B and 13C, there is shown a block schematic diagram of the operational components of the fluid delivery system according to one embodiment of the present invention. The peristaltic pump includes pumping elements or fingers 729 that are manipulated in a pumping sequence in response to rotation of the shaft 727. The output shaft of ultrasonic (U/S) motor 800 is coupled to the pump shaft 727 that carries an optical encoder disk 802. The optical sensing element 801 detects peripheral marks and an index mark for producing outputs indicative of disk position and speed of rotation. These outputs are supplied to the controller 71 that also receives control signals from manual-entry keyboard 48 and from pressure sensors 717, 719, bubble detector 718 and access door safety switch 716. The controller 71 generates multiphasic drive signals via drive circuit 69 and, among other functions, also controls the display 53, alarm indicators, and the like.

Figure 15A:
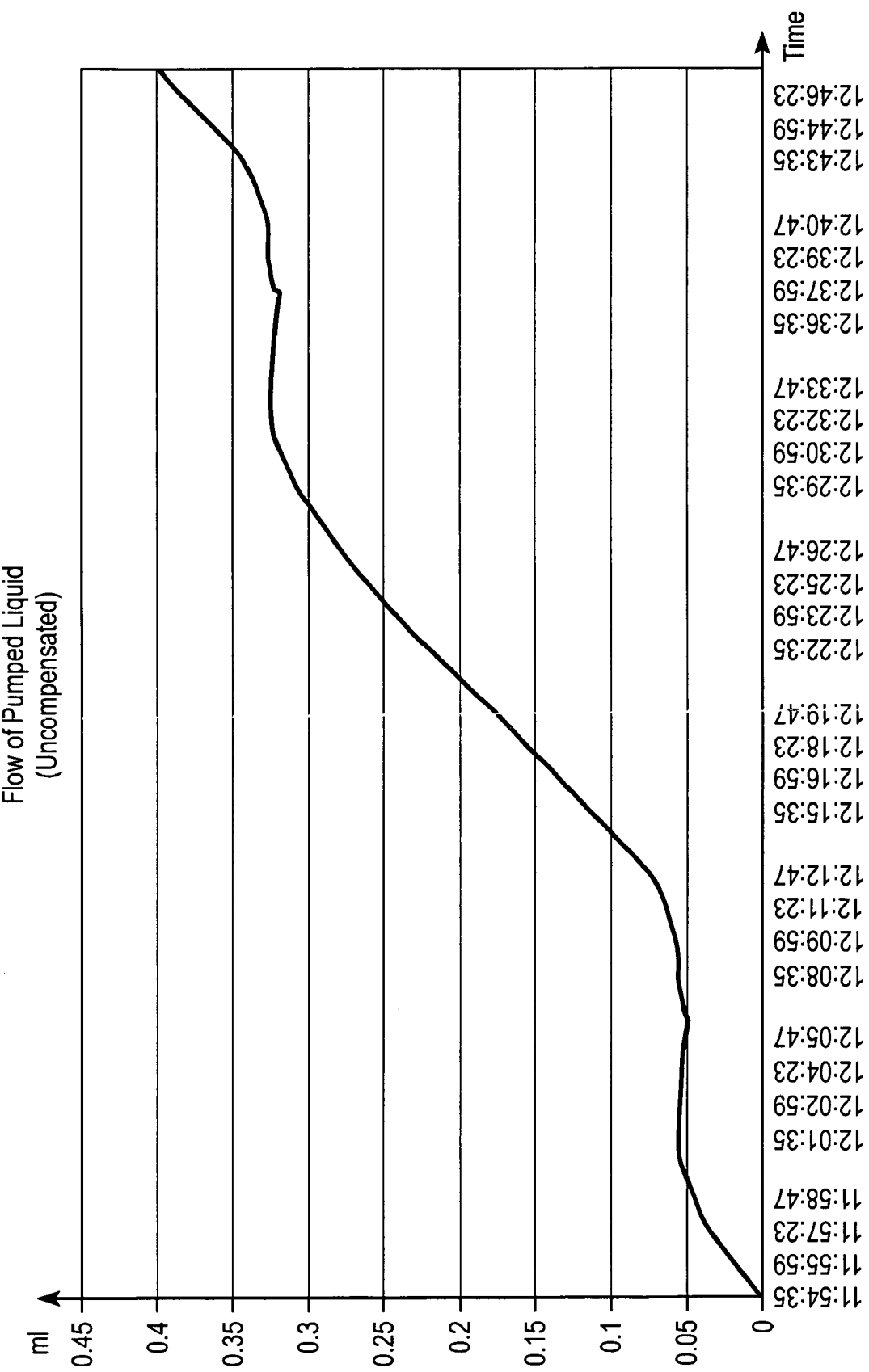
FIG. 15A is a chart illustrating typical flow rate through a linear peristaltic pump operating at constant speed.

For proper operation, the linear peristaltic pump mechanism requires a high degree of control in order to assure accuracy and linearity of fluid flow rate. The operating speed of the pump shaft is modulated to overcome flow-rate non-linearities or discontinuities commonly experienced within a peristaltic pumping cycle, as illustrated in the chart of FIG. 15A, of fluid flow rate over time at constant shaft speed. For this reason, the controller 71 requires signal information indicative of the exact location of pump elements during the interval of a pumping cycle in order to determine requisite speed modulation and when to apply the speed modulation during a pumping cycle. FIG. 15A shows the uncompensated flow output of the peristaltic pump according to one embodiment operating at a very slow RPM rate, over slightly more than one revolution (one cycle of 12 pump fingers) that takes about 31 minutes and delivers about 0.32 ml of fluid. It should be noted that there exists a no-flow "dead band" of approximately 11 minutes in the 31 minute cycle, including a small discontinuity. The discontinuity is dependent on very small mechanical tolerances such as the lengths of the fingers, the perpendicularity of the platen to the fingers, and the likes which vary pump to pump. However, the long 11-minute dead band is very similar pump to pump.

In accordance with the present invention, very fine control of pump-flow characteristics is established utilizing modulation of the rotational speed during each cycle of the peristaltic mechanism. The resultant flow, as illustrated in the graph of FIG. 15B resembles the smoothness and linearity of syringefine pumps, a desirable characteristic when infusing potent drugs or infusing small patients, i.e., babies.

Figure 15B:
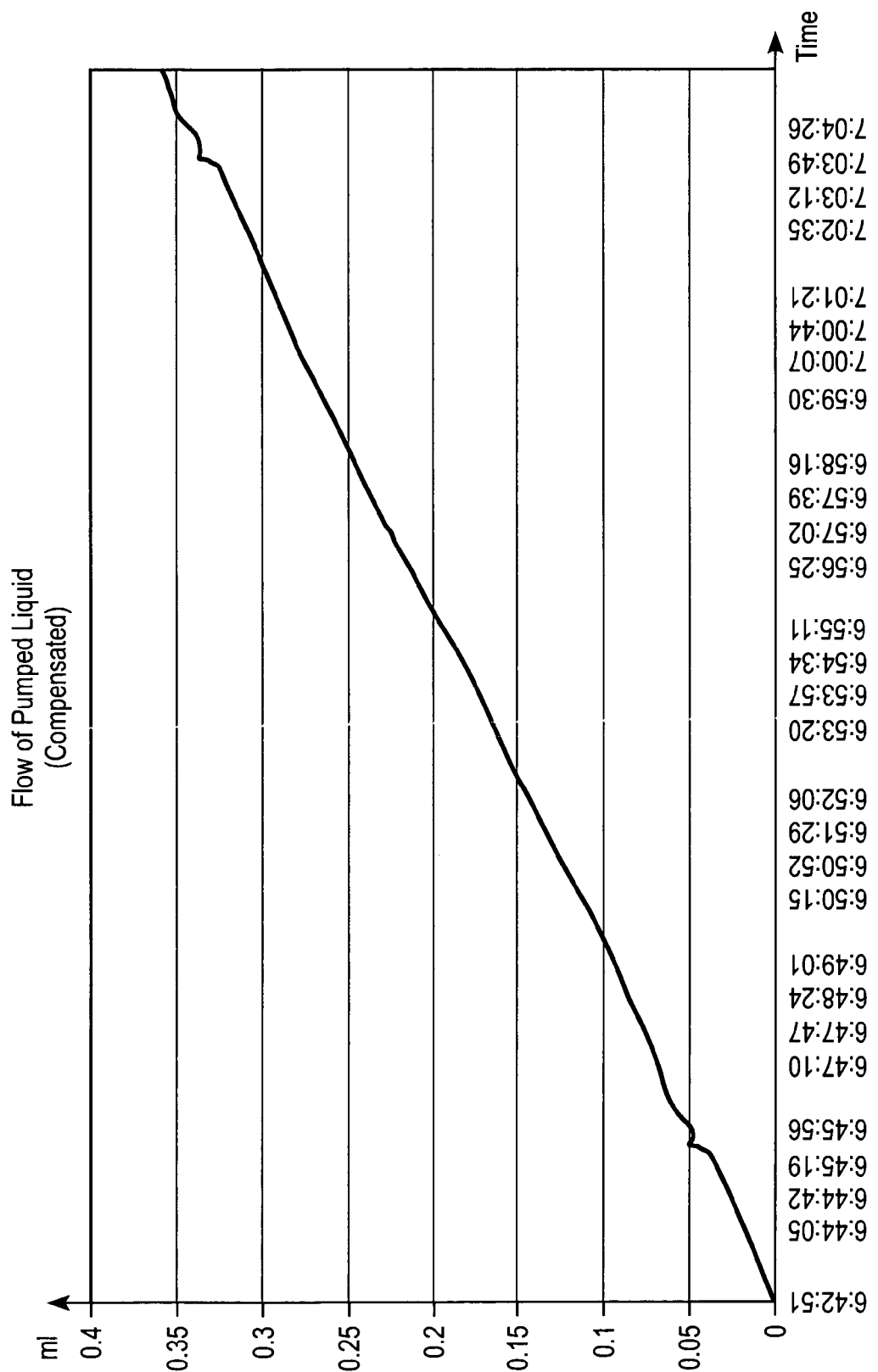
FIG. 15B is a chart illustrating flow rate through a linear peristaltic pump operating in compensated manner in accordance with an embodiment of the present invention.

Specifically, FIG. 15B shows the flow output of the pump resulting from speed 'modulation' applied to each rotation, in accordance with the present invention. The rotational speed modulation is accomplished using, for example, 8 discrete different speeds of the motor and pump during the dead band interval. To accomplish such speed modulation for flow correction, the drive motor 800 must be able to start and stop very quickly and in very small angular displacement typically in the range from about 3 to about 10 milliseconds, and within about 0.3 to about 0.9 degrees of arc. The encoder 801, 802 outputs of index and 1000 pulses per revolution indicate to the controller 71 the starting position of the dead band (index plus mechanical offset by number of pulses counted) for compensation and the exact (i.e., the rotational distance as pulses counted) to control timing and application of the discrete speeds. After compensation is applied in this way, according to the present invention, the flow output of the linear peristaltic pump is very linear in delivering very precise amounts of fluid of about 1 ml/Hr. The lowest pump rate (1 ml/HR) is a basis for compensation as at high speeds the dead band is inherently shorter and less consequential.

The optical encoder 801, 802 provides both fine and coarse output indications of the disk position and speed of rotation. Specifically, one index mark is sensed to identify the exact angular position of the pump shaft 727, and numerous peripheral graticule marks (e.g., 1000 about the periphery) provide fine indication of angular re-positioning of the shaft relative to the index mark. Of course, the frequency of recurrence of sensed graticule marks also indicates rotational or angular speed of shaft 727. Thus, the controller 71 receives control signals from the optical encoder 801, 802 that facilitate modulation of motor speed in the manner as described above to overcome discontinuities or anomalies in a selected flow rate of fluid through the peristaltic pump as illustrated in FIG. 15B, during portions of the pump cycle driven by the ultrasonic motor 800.

Figure 14:
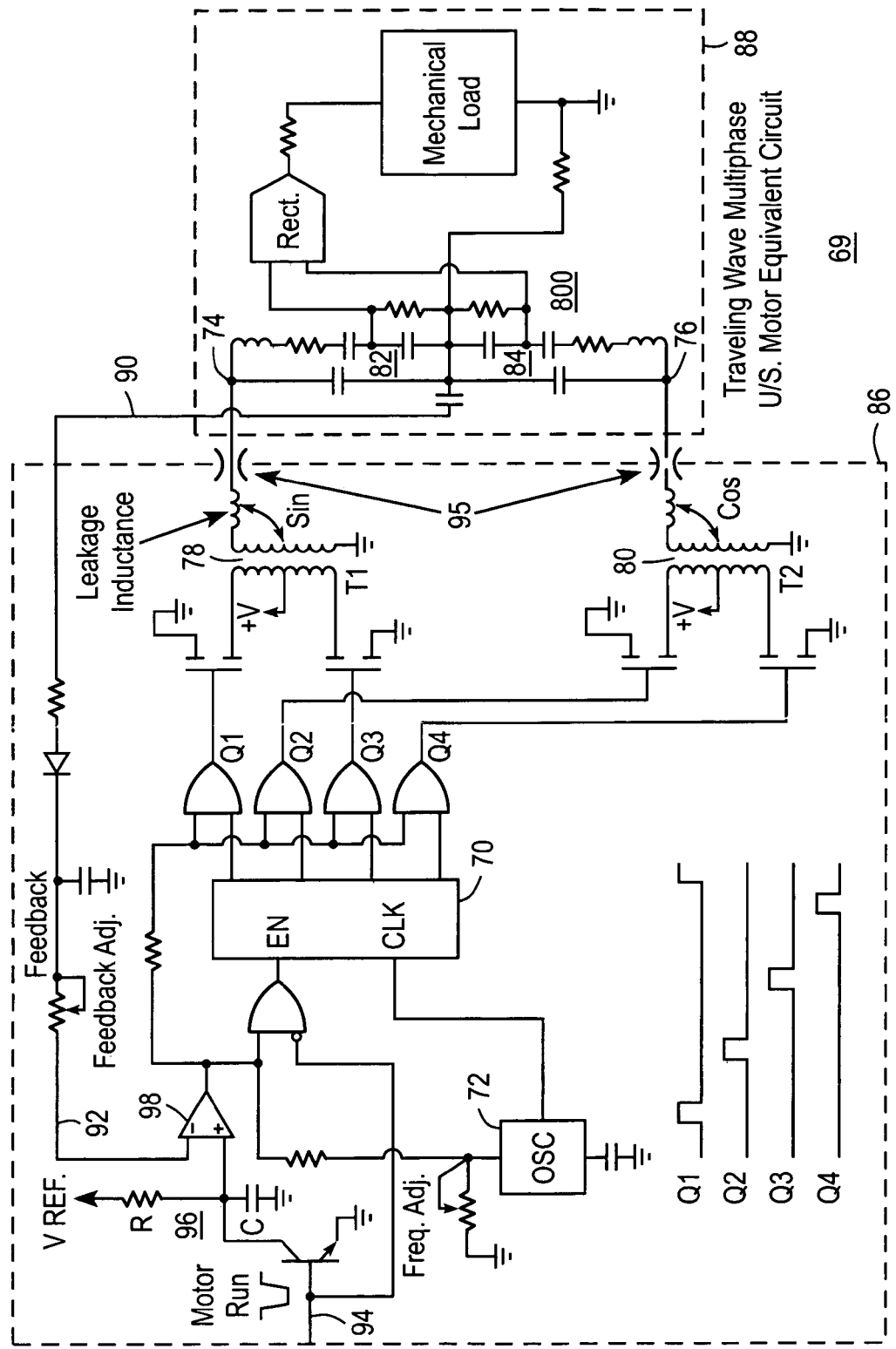
FIG. 14 is a schematic diagram of drive circuitry for a multiphasic u/s motor in accordance with one embodiment of the present invention.

In order to accomplish fine resolution of fluid flow rates through the peristaltic pump, the drive motor 800 must be able to start and stop very rapidly, typically within the range of about 3 to 10 milliseconds. The driving ultrasonic signals are generated by the drive circuit 69 at about 43 KHz with very low harmonic content in the range of about 6 or 8 MHz to about 130 MHz within which MR scanners are sensitive to RF signals. This is accomplished on the drive circuit 69, as shown in the schematic diagram of FIG. 14, using a shift-register type of counter 70 that receives input from voltage-controlled oscillator 72 to generate high-voltage ultrasonic frequencies in sine and cosine relationship 74, 76. Coreless or air core transformers 78, 80 are driven push-pull through field-effect power transistors that receive paired outputs from the register 70. The primary inductance (through the turns ratio) and the leakage inductance of these transformers 78, 80 coact with the characteristic input capacitance 82, 84 of the ultrasonic motor 800 to produce substantially sinusoidal, high-voltage drive signals 74, 76 of low harmonic content. These sinusoidal drive signals also pass efficiently through the filters 95 from the electrically shielded controller section 86 to the electrically shielded motor section 88, and exhibit concomitant low to negligible RF interference attributable to drive signal harmonics.

It should be noted that the ultrasonic motor 800 provides an AC signal 90 representative of the composite sine and cosine drive signals. This AC signal 90 is rectified and integrated or low-pass filtered to produce a DC voltage level 92 that is indicative of motor speed, and is distinguishable from the position and rotational speed indications digitally derived from the optical encoder 801, 802. The analog DC voltage level 92 is applied via the operational amplifier 98 to the voltage-controlled osullator 72 in order to control the frequency of the motor drive signals. Specifically, the rotational speed of the ultrasonic motor 800 varies inversely with frequency of the drive signals. Accordingly, an applied 'motor run' signal 94 in combination with the DC feedback voltage 92 and the time constant of the R and C filter 96, cause the drive circuit 69 to generate drive signals 74, 76 that sweep in frequency from a slightly higher initial frequency that is useful for starting the motor 800 from standstill to an appropriate running frequency that establishes a steady-state motor speed.

Alternatively, the drive signals, 74, 76 for the ultrasonic motor 800 may be generated from combined signals Q1/Q3, and Q2/Q4 through suitable filtering to generate low voltage sinusoidal sine and cosine signals. These signals may then be amplified to sufficient level (typically about 100 Volts RMS) to drive the ultrasonic motor 800.

Figure 16:
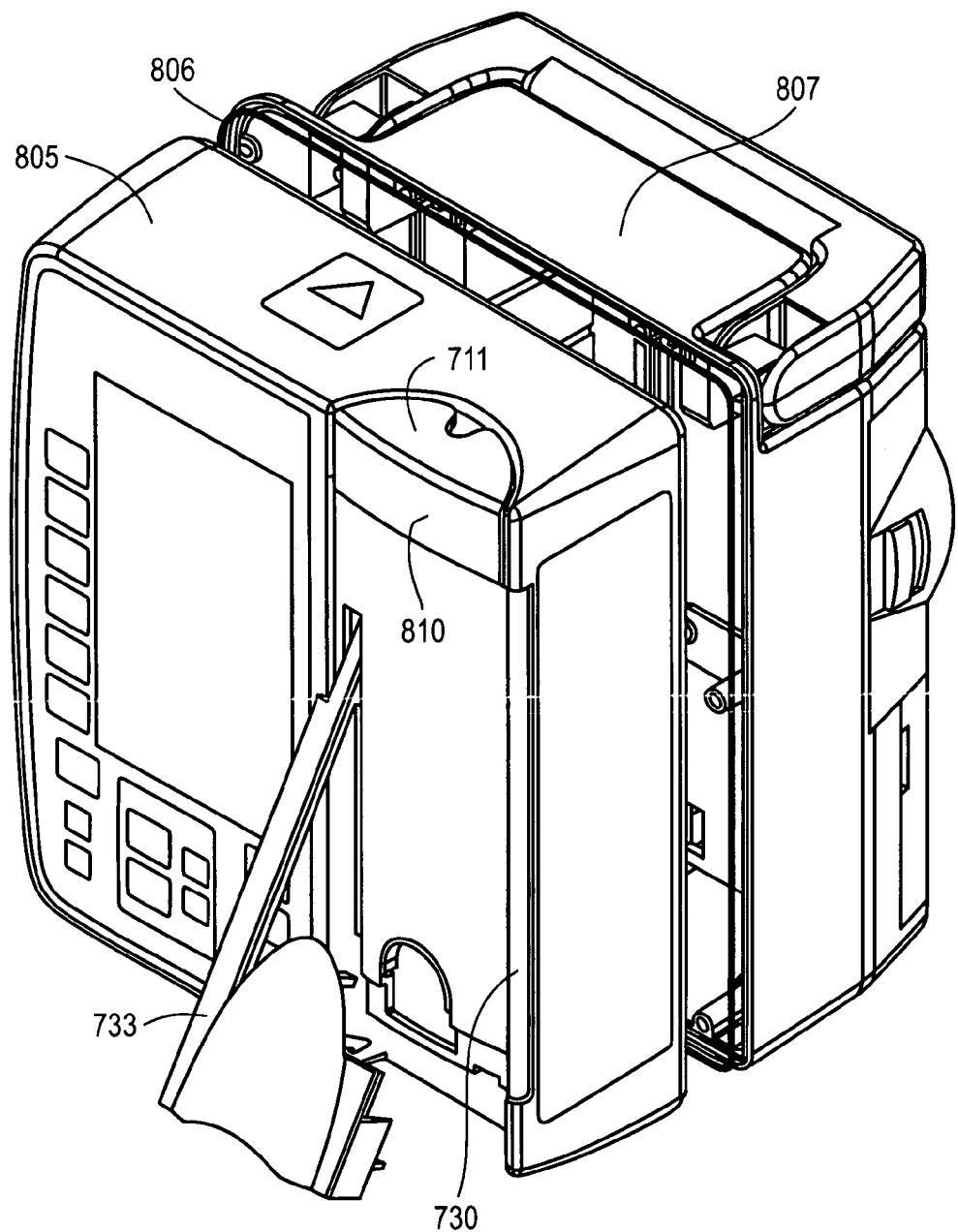
FIG. 16 is an exploded perspective view of a pump unit according to the present invention.
Figure 17:
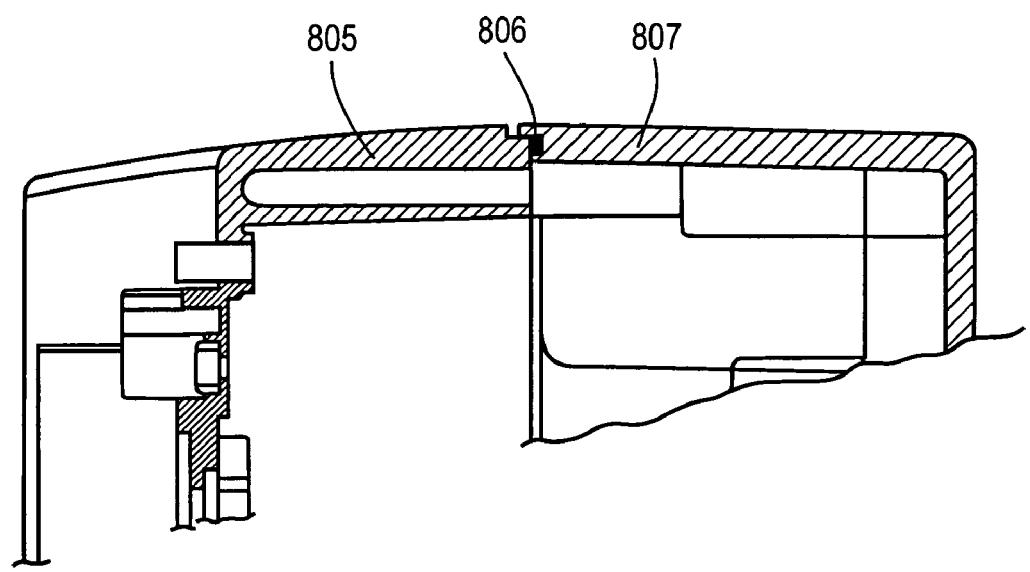
FIG. 17 is a partial sectional view of a gasket disposed between housing segments.

Referring now to FIG. 16, there is shown an exploded perspective view of one embodiment of the pump unit 406 of the present invention in which a gasket 806 is disposed between mating segments 805, 807 of the housing. The gasket 806 is formed of a flexible and electrically conductive material to form a fluid-tight seal between the housing segments 805, 807 as shown in the sectional view of FIG. 17. The conductive gasket 806 also inhibits internally-generated RF noise signals from radiating out of the conductive housing segments 805, 807. The conductive housing segments 805, 807 thus form an integral shield that prevents radiative electronic signals from emanating from internal circuitry, for example as illustrated in FIG. 13, and additionally protects such internal circuitry from fluid spills that might be detrimental to reliable operation.

Figure 18:
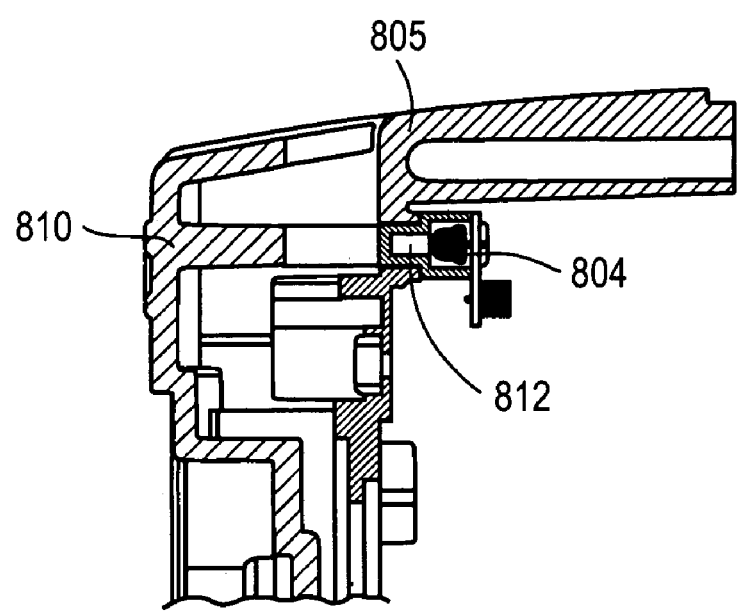
FIG. 18 is a partial cross sectional view of annunciator lights according to the present invention; and, FIG. 19 is a front view of the pump unit of FIG. 16.
Figure 19:
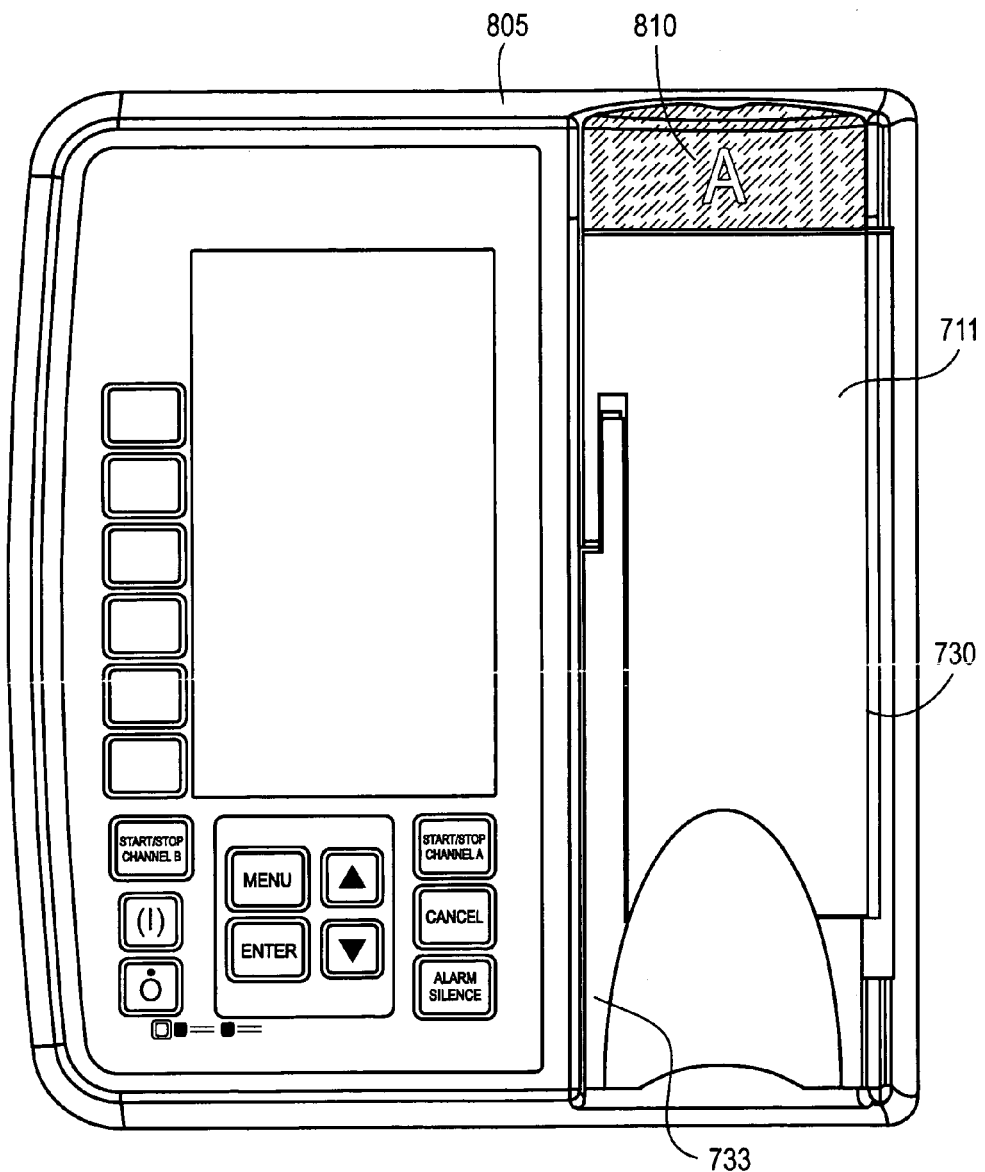

Referring now to the sectional view of FIG. 18, there is shown one light source such as light-emitting diode 804 of a plurality of such light sources and different colors that are lineally disposed within the housing segment 805 near a top edge thereof. These light sources are positioned behind the door 711 of conductive material that is hinged 730 along an outer edge of the housing segment 805 to facilitate easy access to the peristaltic pumping structure that is supported therein. The door 711 includes a locking lever 733 for securely closing the door 711 in operational position against a length of tubing 703, as illustrated and previously described herein with reference to FIG. 7. The door 711 also includes a clear or translucent window 810, as illustrated in FIGS. 18, 19, in alignment with the light sources 804 to provide large-area illumination for easy visualization from a distant location of the light from a source 804. A light-scattering element or light pipe 812 may be disposed intermediate the light sources 804 and the window 810 to provide more uniform illumination over the area of the window 810 in known manner. Thus, a light source 804 of green color may pulse on and off recurring during normal pumping operation, and a light source of red color may pulse on and off recurring to indicate an alarm condition, all for convenient visualization from a distant location. And the light sources 804 are sufficiently recessed within the conductive housing segment 805 to inhibit radiative RF noise signals from emanating from the housing.

Therefore, the liquid infusion apparatus of the present invention promotes easy replacement or substitution of pumping devices without interrupting patient connection or otherwise comprising sterility of an installed infusion system. An infusion set includes integral segments of a liquid conduit and operable components for interaction and operational engagement with associated components of a pumping device that is compatible with an MRI environment. Ultrasonic motor drive signals are generated with low harmonic content using efficient step-up transformer that co-act with the characteristic input impedance of the ultrasonic motor to shape signals as sinusoidal waveforms of low harmonic content.

What is claimed is:

1. An infusion apparatus having drive circuitry for an ultrasonic motor, comprising:
   an oscillator that generates an output at a frequency;
   a circuit connected to receive the output from the oscillator to produce recurring output pulses at spaced intervals on a plurality of output terminals;
   a pair of air-core transformers, each having a secondary winding to connect to the ultrasonic motor, and having a pair of primary windings to conduct current therethrough in alternating relationship in response to output pulses from separate ones of pairs of the plurality of output terminals; and
   a cam shaft coupled to the ultrasonic motor, the cam shaft further coupled to a plurality of pump elements, wherein rotation of the cam shaft by the ultrasonic motor manipulates the plurality of pump elements to adjust a pinch point along a tubing, thereby controlling an infusion fluid flow rate.

2. Drive circuitry according to claim 1 in which the circuit produces recurring pulses at substantially equal successive delays sequentially on four output terminals; and
   conduction of current in each of the pair of primary windings on one of the pair of transformers is controlled in response to output pulses appearing on first and third of the four output terminals, and conduction of current in each of the pair of primary windings on another of the pair of transformers is controlled in response to output pulses appearing on second and fourth of the four output terminals for applying drive signals to the ultrasonic motor of substantially sinusoidal wave forms.

3. Drive circuitry according to claim 2 for an ultrasonic motor having a capacitive component in the characteristic input impedance, and in which inductance of a transformer and capacitive component of the characteristic input impedance of the motor coact at ultrasonic operating frequencies to apply to the motor a pair of phase-displaced drive signals of substantially sinusoidal wave forms.

4. Drive circuitry according to claim 1 including a charging circuit to generate a control signal applied to the oscillator to selectively control change of frequency thereof during a charging interval of the charging circuit.

5. Drive circuitry according to claim 1 in which the ultrasonic motor produces an electrical feedback signal representative of the speed of the motor, the drive circuitry including a feedback circuit that forms a DC voltage level from the electrical feedback signal representative of the speed of the motor for application to the oscillator to control the operating frequency thereof.

6. Drive circuitry according to claim 2 including switching elements connected to each of the primary windings of each of the transformers to control conduction of current therethrough in response to control signals applied thereto;
   the switching elements connected to a pair of primary windings on one transformer being connected to receive as control signals, respectively, output pulses appearing on first and third of the four output terminals; and
   the switching elements connected to a pair of primary winding on another of the transformers being connected to receive as control signals, respectively, output pulses appearing on second and fourth of the four output terminals.

7. The infusion apparatus of claim 1, further comprising an infusion fluid flow rate control circuit that activates a drive signal of the ultrasonic motor; detects an amount of angular displacement of the cam shaft; deactivates the drive signal after a specified angular displacement is detected; and waits for a specified period of time before the drive signal is activated again.

8. The infusion apparatus of claim 7, wherein the detected angular displacement of the cam shaft is less than about 0.9 degrees of arc.

9. The infusion apparatus of claim 7, wherein the period of time before the drive signal is activated varies with an angular position of the cam shaft.

10. The infusion apparatus of claim 7, wherein the drive signal of the ultrasonic motor is activated for less than about 10 milliseconds.

11. The infusion apparatus of claim 7, wherein the flow rate control circuit provides volumetric flow rate of the infusion fluid that is substantially linear.

* * * * *

UNITED STATES PATENT AND TRADEMARK OFFICE
CERTIFICATE OF CORRECTION

PATENT NO. : 7,553,295 B2  Page 1 of 1
APPLICATION NO. : 11/271705
DATED : June 30, 2009
INVENTOR(S) : Roger E. Susi It is certified that error appears in the above-identified patent and that said Letters Patent is hereby corrected as shown below:

In Column 9, Line 32 change "MRI-comptabile" to --MRI-compatible--.

In Column 12, Line 2 change "receptable" to --receptacle--.

In Column 14, Line 4 change "osullator" to --oscillator--.

In Column 14, Line 66 change "comprising" to --compromising--.

In Column 15, Line 5 change "transformer" to --transformers--.

Signed and Sealed this

Second Day of February, 2010

David J. Kappos
*Director of the United States Patent and Trademark Office*